United States Patent
Wang et al.

(10) Patent No.: US 7,820,426 B2
(45) Date of Patent: Oct. 26, 2010

(54) BIONANOMATERIALS AND THEIR SYNTHESIS

(75) Inventors: Qian Wang, Columbia, SC (US); Zhongwei Niu, Columbia, SC (US)

(73) Assignee: University of South Carolina, Columbia, SC (US)

(*) Notice: Subject to any disclaimer, the term of this patent is extended or adjusted under 35 U.S.C. 154(b) by 0 days.

(21) Appl. No.: 12/090,579

(22) PCT Filed: Nov. 1, 2006

(86) PCT No.: PCT/US2006/042363

§ 371 (c)(1),
(2), (4) Date: Oct. 9, 2008

(87) PCT Pub. No.: WO2007/120193

PCT Pub. Date: Oct. 25, 2007

(65) Prior Publication Data

US 2009/0029441 A1    Jan. 29, 2009

Related U.S. Application Data

(60) Provisional application No. 60/732,279, filed on Nov. 1, 2005, provisional application No. 60/815,499, filed on Jun. 21, 2006.

(51) Int. Cl.
*C12N 7/00* (2006.01)
*C12N 1/00* (2006.01)
*B82B 3/00* (2006.01)

(52) U.S. Cl. .................. 435/235.1; 435/317.1; 57/295; 977/762

(58) Field of Classification Search ........................ None
See application file for complete search history.

(56) References Cited

U.S. PATENT DOCUMENTS

2005/0180992 A1* 8/2005 Belcher et al. ........... 424/204.1

OTHER PUBLICATIONS

Numata, et al. β-1,3-Glucan (Schizophyllan) Can Act as a One-Dimensional Host for Creation of Novel Poly(aniline) Nanofiber Structures. Org. Lett. 2004; 6(24): 4447-4450.*

Baughman et al., "Carbon Nanotubes—the Route Toward Applications", Science, Aug. 2002, vol. 297, pp. 787-792.

Cui et al., "Functional Nanoscale Electronic Devices Assembled Using Silicon Nanowire Building Blocks", Science, Feb. 2001, vol. 291, pp. 851-853.

Douglas et al., "Host-Guest Encapsulation of Materials by Assembled Virus Protein Cages", Nature, May 1998, vol. 393, pp. 152-155.

Douglas et al., "Viruses: Making Friends with Old Foes", Science, May 2006, vol. 312, pp. 873-875.

Flynn et al., "Viruses as Vehicles for Growth, Organization and Assembly of Materials", Acta Materialia, Aug. 2003, vol. 51, pp. 5867-5880.

(Continued)

*Primary Examiner*—Mary E Mosher
*Assistant Examiner*—Stuart W Snyder
(74) *Attorney, Agent, or Firm*—Dority & Manning, P.A.

(57) ABSTRACT

The use of biomaterials, such as viruses and virus-like particles, to form nanostructures is generally disclosed. For instance, rod-like viruses can be used to form composite nanofibers that are fixed together in a head-to-tail assembly by a polymer. Also, 2-dimensional nanostructures formed from crosslinked viruses assembled in a single, film-like layer are generally disclosed. Porous gels having controllable pore size through the use of virus particles are also disclosed.

27 Claims, 17 Drawing Sheets

(a) AFM height image of wild type TMV and (b) corresponding phase image.
(c) AFM height image of a single polyaniline/ TMV composite fiber and (d) corresponding phase image. (All the images have the same scale bar)

OTHER PUBLICATIONS

Fowler et al., "Tobacco Mosaic Virus Liquid Crystals as Templates for the Interior Design of Silica Mesophases and Nanoparticles", Advanced Materials, Aug. 2001, vol. 13, pp. 1266-1269.

Huang et al., "Directed Assembly of One-Dimensional Nanostructures into Functional Networks", Science, Jan. 2001, vol. 291, pp. 630-633.

Mao et al., "Virus-Based Toolkit for the Directed Synthesis of Magnetic and Semiconducting Nanowires", Science, Jan. 2004, vol. 303, pp. 213-217.

Melosh et al., "Ultrahigh-Density Nanowire Lattices and Circuits", Apr. 2003, vol. 300, pp. 112-115.

Nam et al., "Virus-Enabled Synthesis and Assembly of Nanowires for Lithium Ion Battery Electrodes", Science, May 2006, vol. 312, pp. 885-888.

Royston et al., "Characterization of Silica-Coated Tobacco Mosaic Virus", Journal of Colloid and Interface Science, Jan. 2006, vol. 298, pp. 706-712.

Russell et al., "Self-Assembly and Cross-Linking of Bionanoparticles at Liquid-Liquid Interfaces", Angewandte Chemie International Edition, Mar. 2005, vol. 44, pp. 2420-2426.

Schlick et al., "Dual-Surface Modification of the Tobacco Mosaic Virus", Journal of the American Chemical Society, Feb. 2005, vol. 127, pp. 3718-3723.

Seeman et al., "Emulating Biology: Building Nanostructures from the Bottom Up", Proceedings of the National Academy of Sciences, Apr. 2002, vol. 99, No. 2, pp. 6451-6455.

Shenton et al., "Inorganic-Organic Nanotube Composites from Template Mineralization of Tobacco Mosaic Virus", Advanced Materials, 1999, vol. 11, No. 3, pp. 253-256.

Wang et al., "Icosahedral Virus Particles as Addressable Nanoscale Building Blocks" Angewandte Chemie International Edition, 2002, vol. 41, pp. 459-462.

Yi et al., "Patterned Assembly of Genetically Modified Viral Nanotemplates via Nucleic Acid Hybridization", Nano Letters, 2005, vol. 5, No. 10, pp. 1931-1936.

* cited by examiner

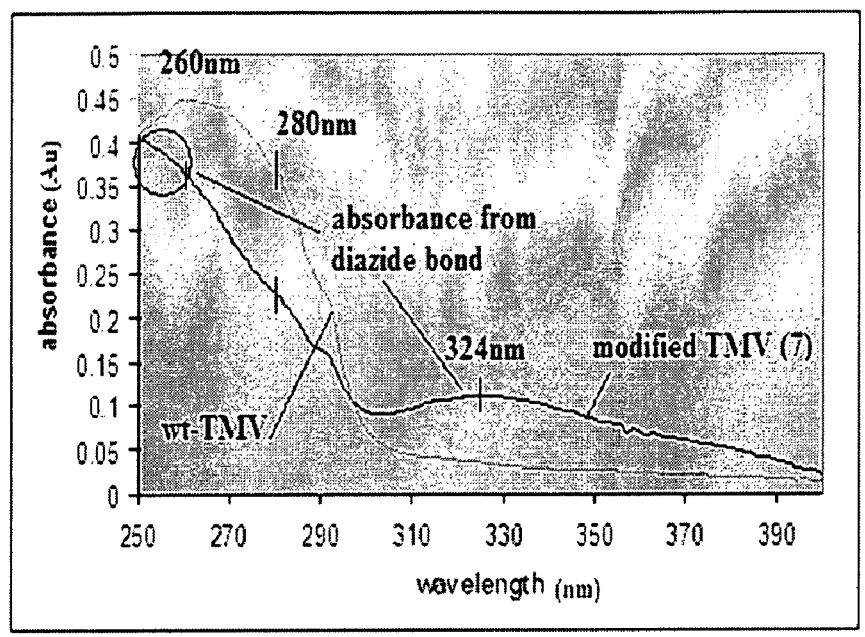
*Figure 5.* UV-vis spectra of native TMV and alkyne modified TMV
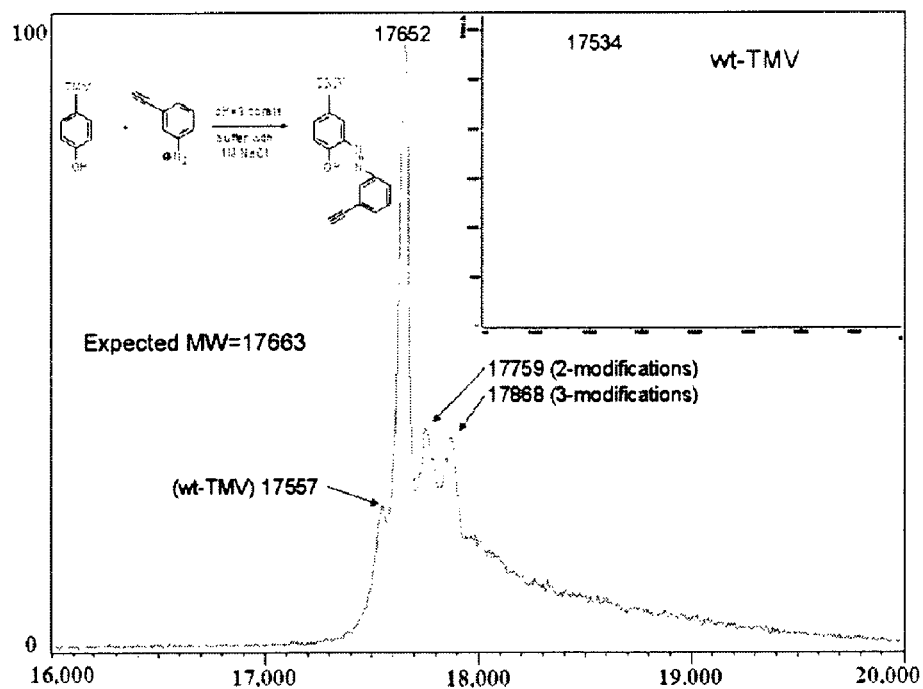
*Figure 6.* MALDI-TOF MS of native TMV and alkyne modified TMV

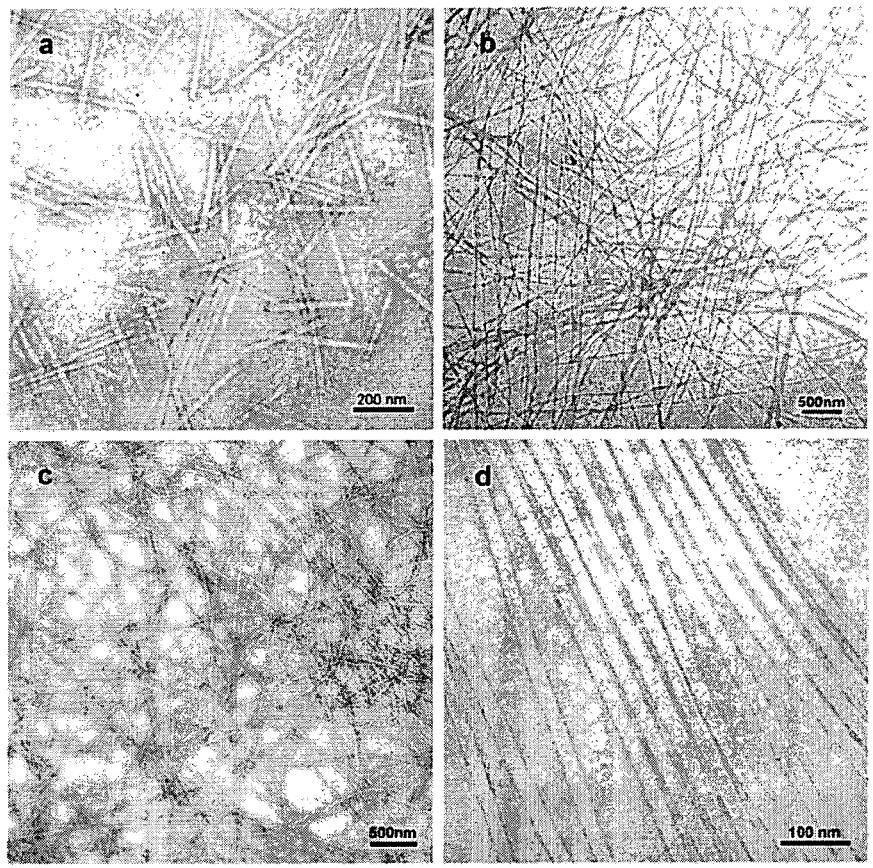
*Figure 7.* TEM images of (a) wild type TMV, (b) 1D polyaniline/TMV composite fibers without negative staining, and (c, d) polyaniline/TMV composite fibers after negative staining.

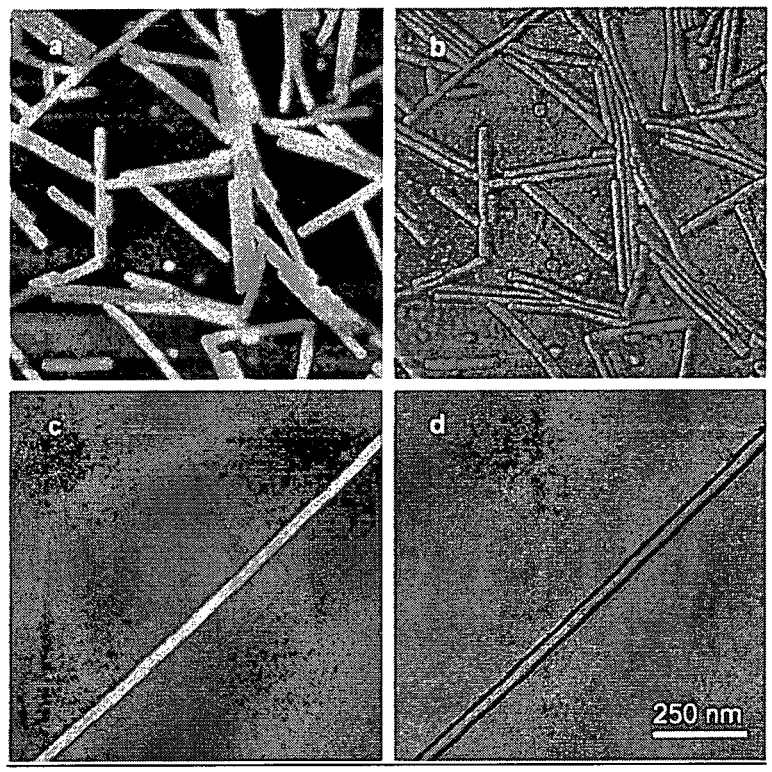
*Figure 8.* (a) AFM height image of wild type TMV and (b) corresponding phase image. (c) AFM height image of a single polyaniline/ TMV composite fiber and (d) corresponding phase image. (All the images have the same scale bar)

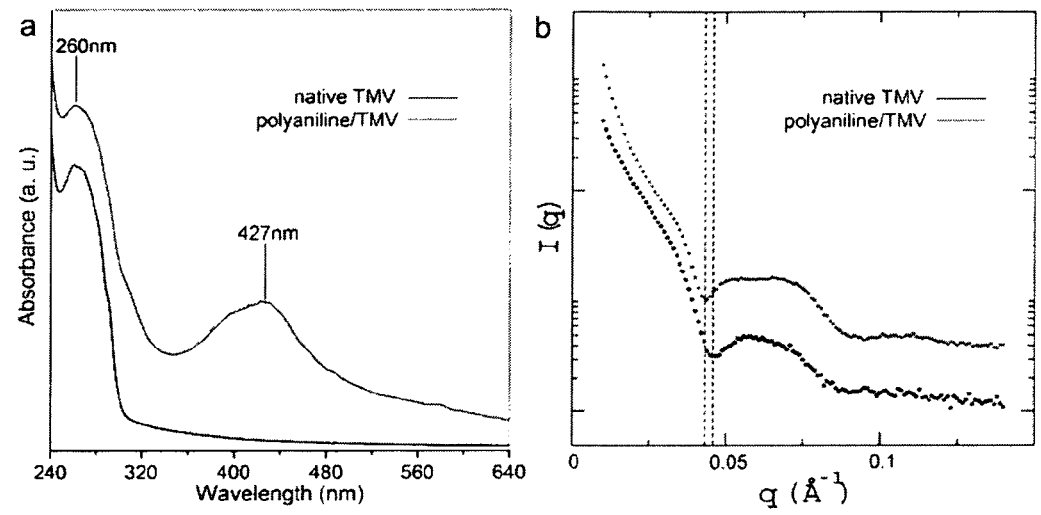
*Figure 9.* (a) UV-vis spectra of native TMV (black) and polyaniline/TMV composite fiber (red). (b) SAXS data of the polyaniline/TMV composite fiber (red) and native TMV (black) dispersed in a silica gel matrix.

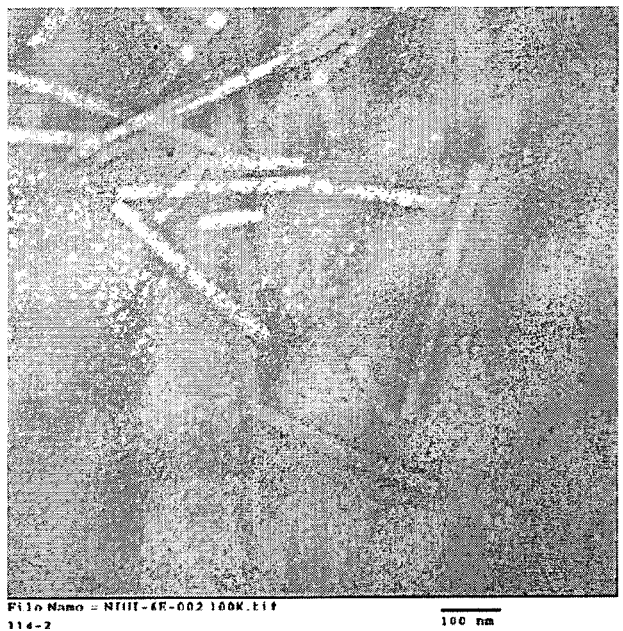
*Figure 10.* TEM images of polyaniline/PSS/TMV composite nanofibers
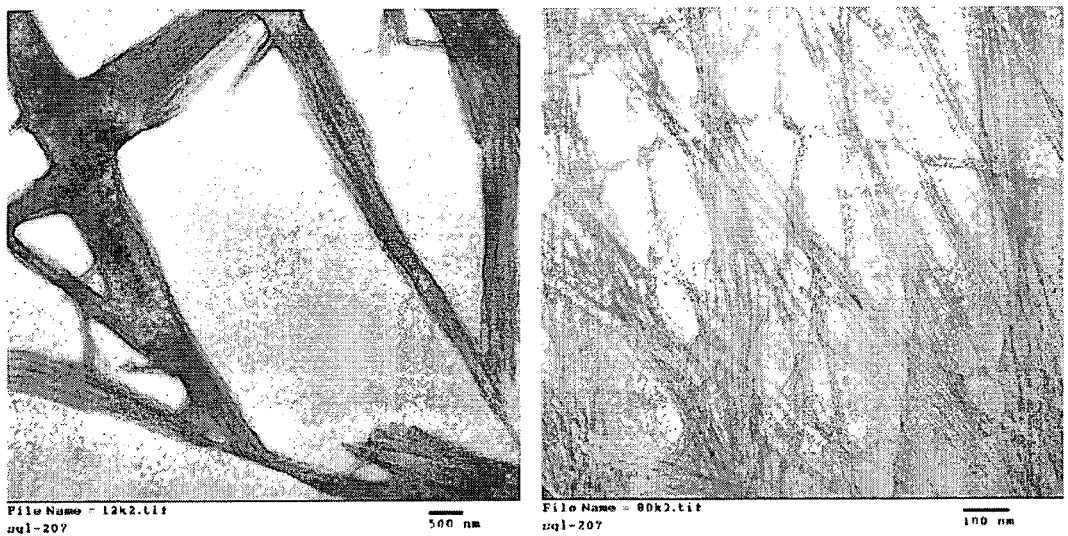
*Figure 11.* TEM images of PEGMA-326/TMV composites.

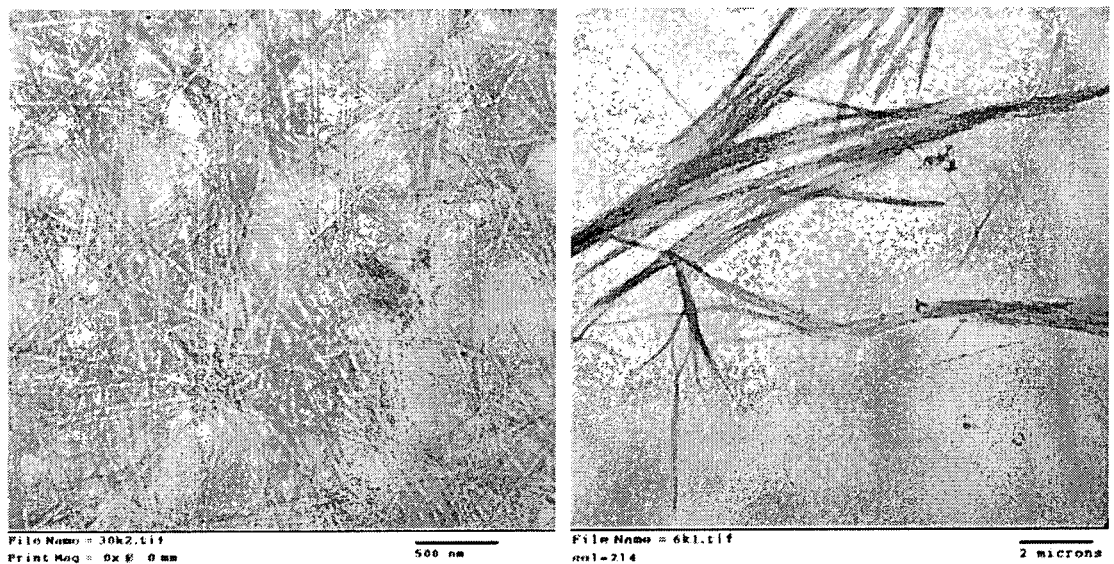
Figure 12. TEM images of EDOT-SO$_3^-$Na$^+$/TMV composites

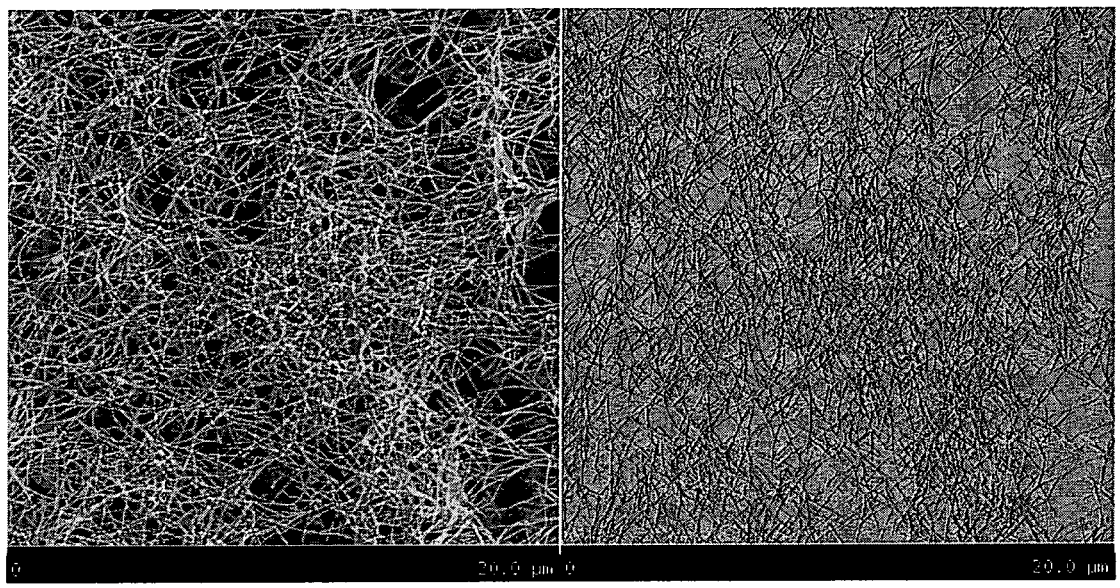
*Figure 13.* AFM height image and phase image of silica/TMV composite fiber
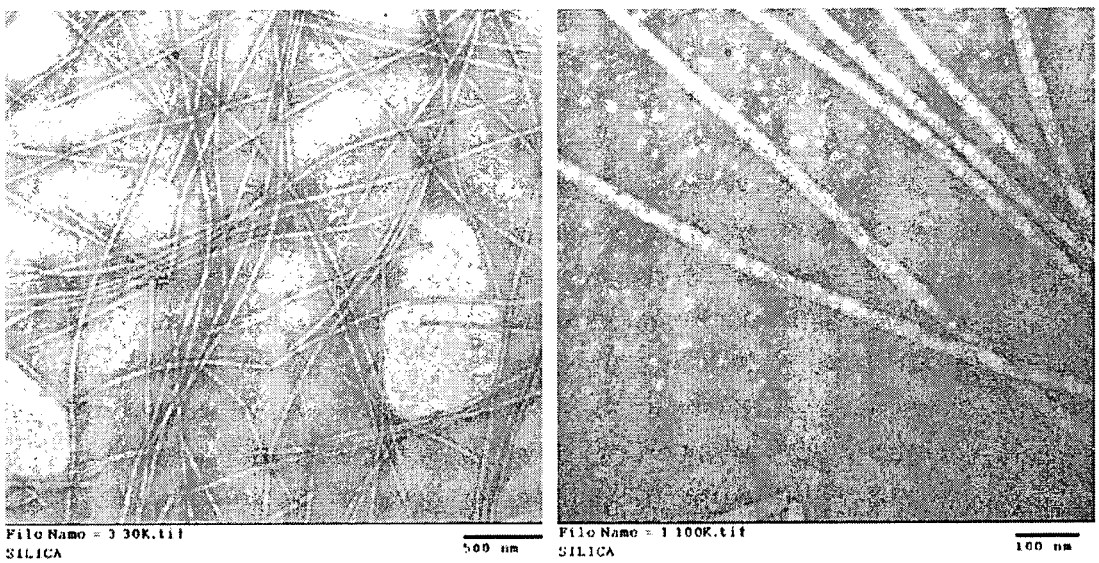
*Figure 14.* TEM images of silica/TMV composite fiber

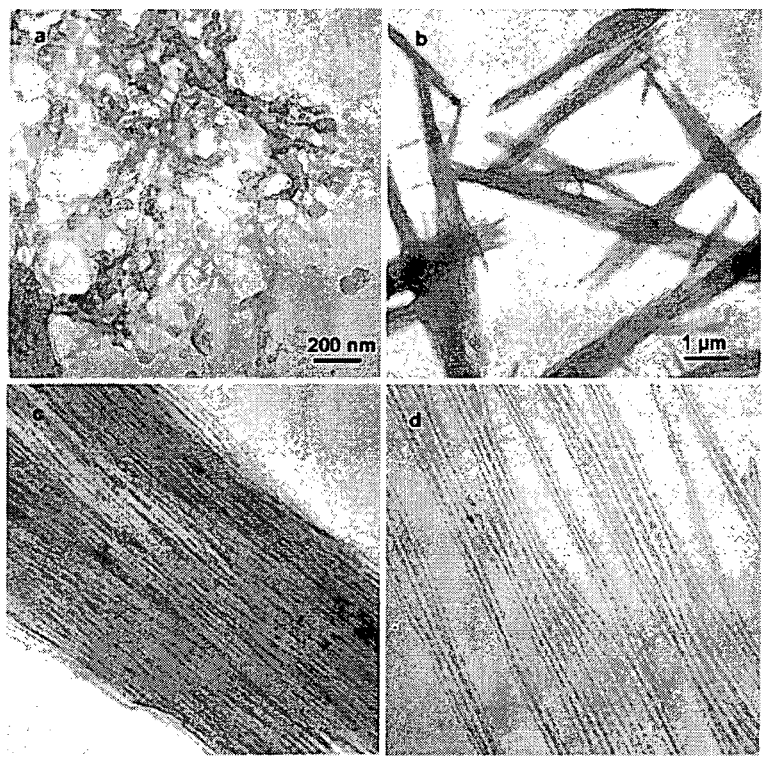
*Figure 15.* TEM images (a) polyaniline/TMV composite at pH 2.5 (b) polyaniline/TMV composite at pH 4 (c) polyaniline/TMV composite at pH 4 (c) polyaniline/TMV composite at pH 6 (Figure 4a, Figure 4c and Figure 4d have the same scale bar)

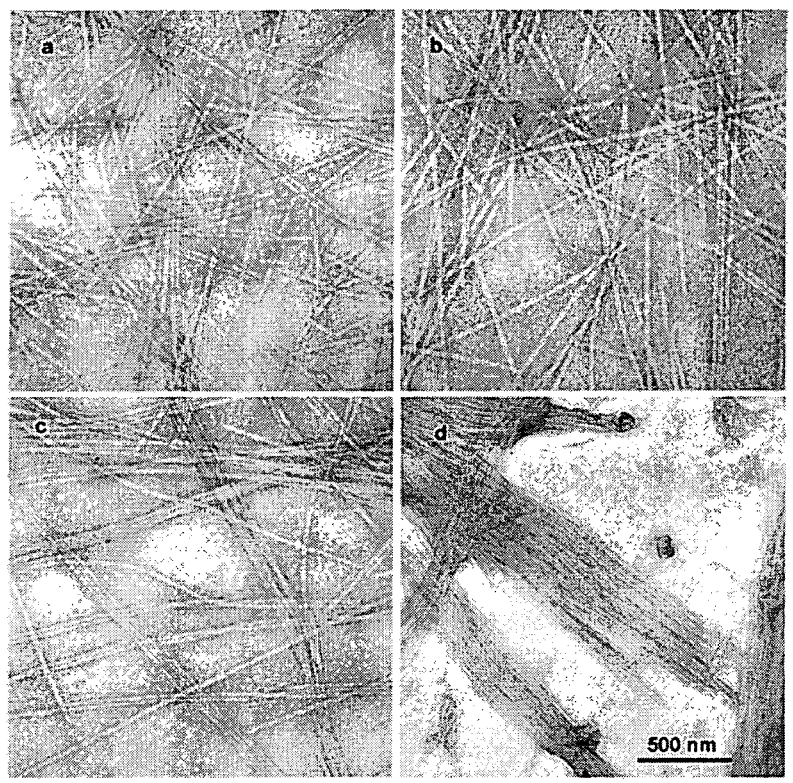
*Figure 16.* TEM images polyaniline/TMV composites at pH 4 with different reaction time (a) 30min. (b) 1h. (c) 2h. (d) 4h.

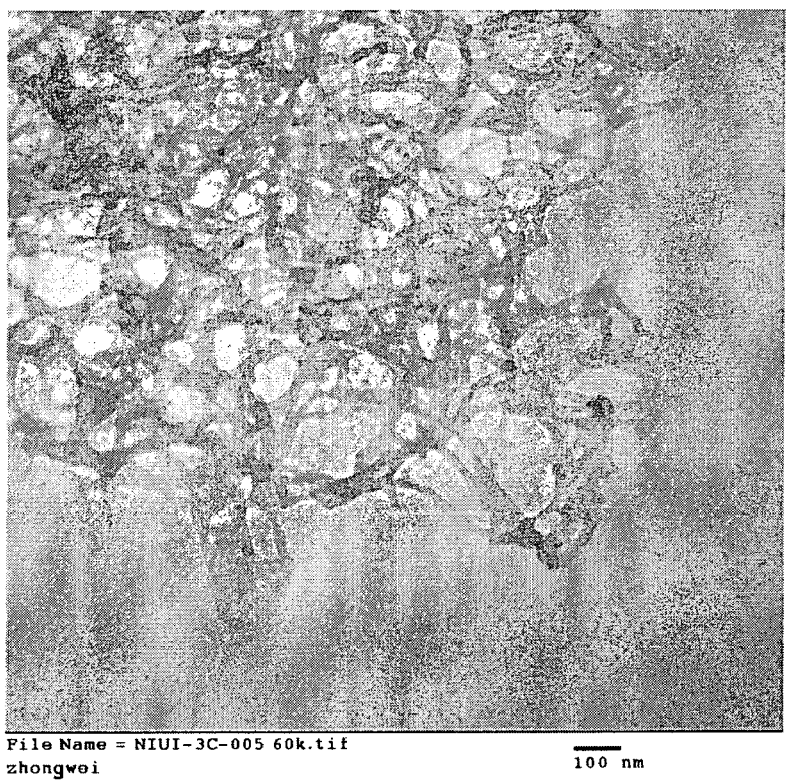
*Figure 17.* TEM image of emeraldine·HCl nanofibers synthesized by seeding the reaction using the TMV

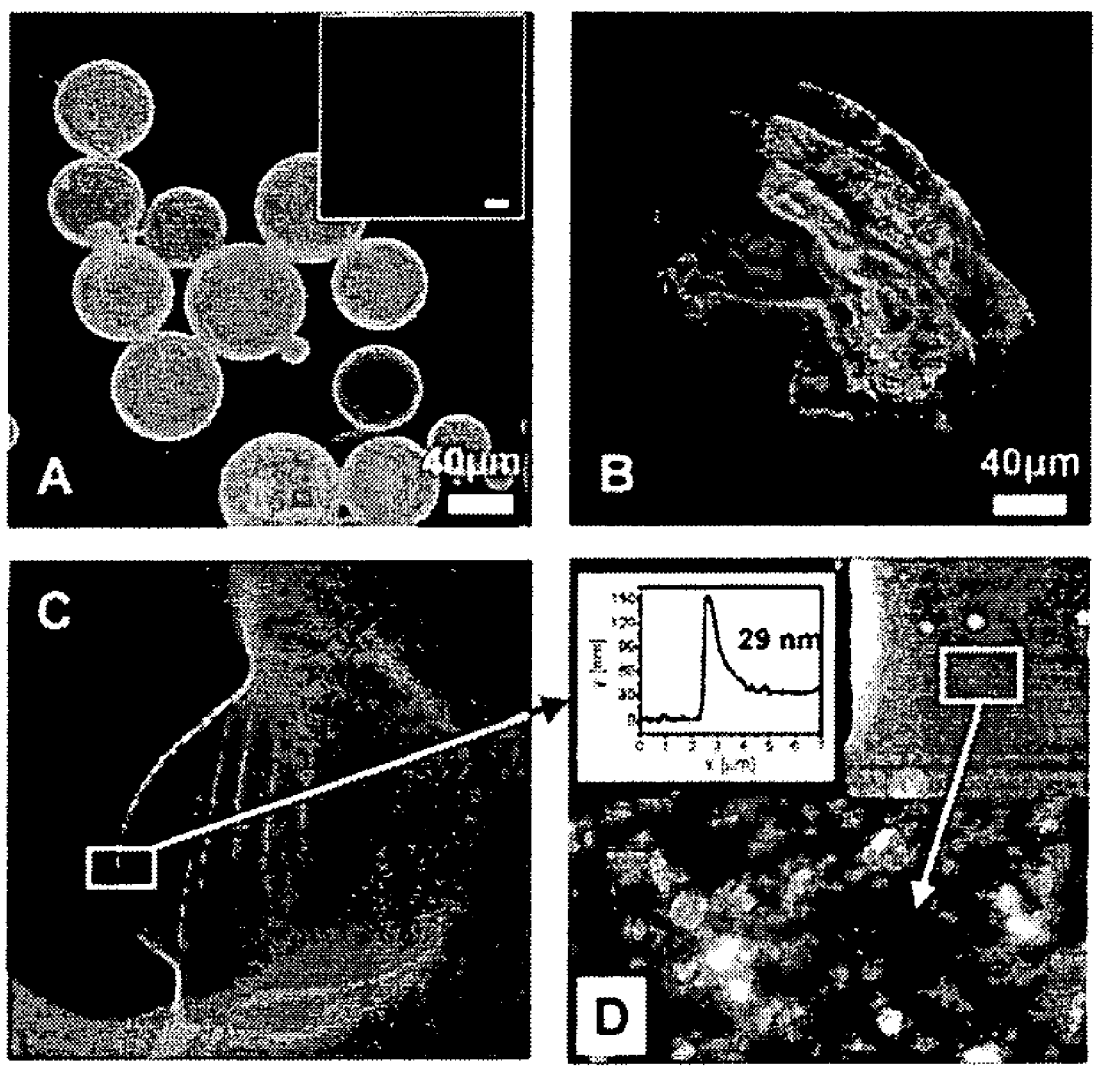
*Figure 18.* Confocal fluorescence microscope and SFM image of CPMV assembly stabilized droplets after cr

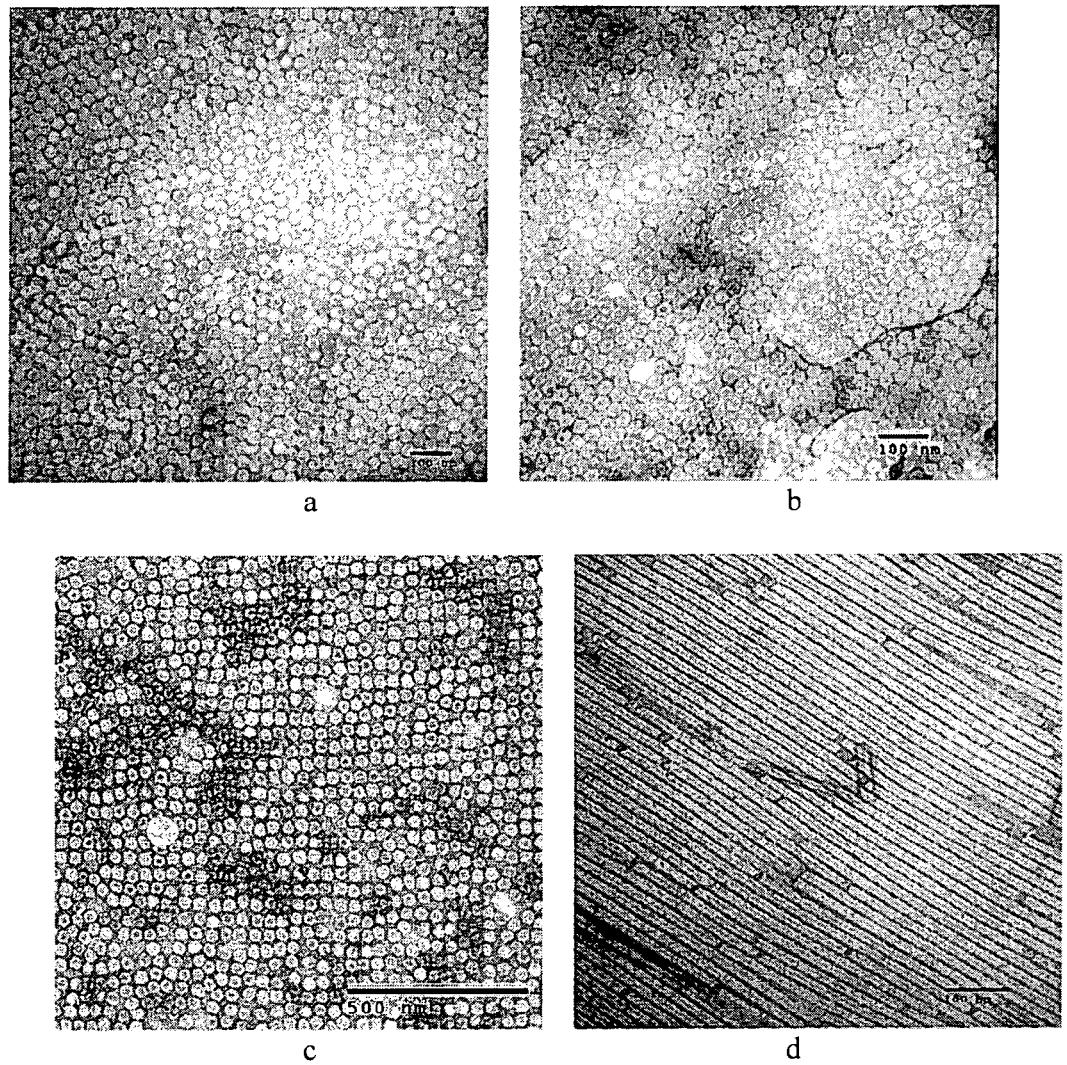
*Figure 19.* TEM images for the 2D ordered arrays of BNPs: (a) the hexagonal array of wt-CPMV, (b) the hexagonal array of wt-TYMV, (c) the square array of wt-CPMV, (d) the parallel array of wt-TMV.

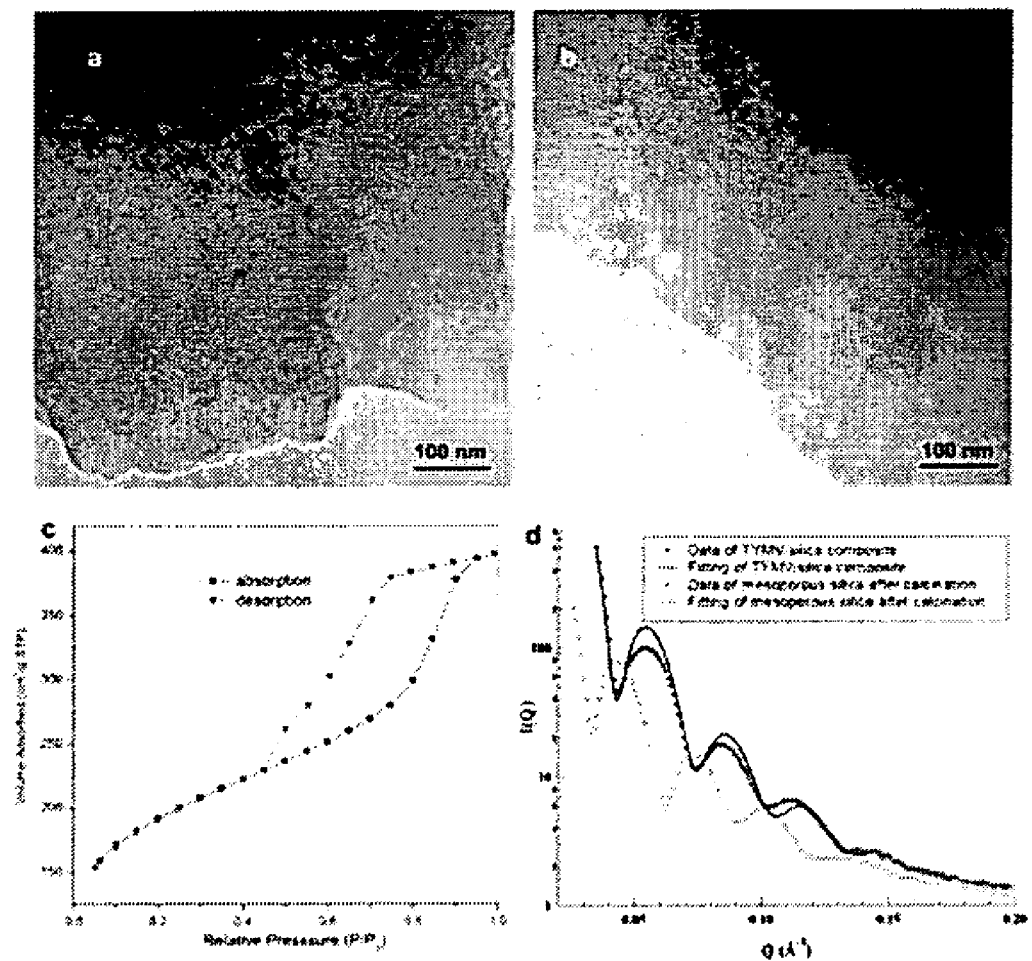
*Figure 21.* TEM images of (a) TYMV/silica composite, and (b) mesoporous silica after calcination at 500 °C for two hours. (c) Nitrogen adsorption-desorption isotherms for TYMV templated mesoporous silica. (d) SAXS data of TYMV/silica composite and mesoporous silica after removal of TYMV by calcination.

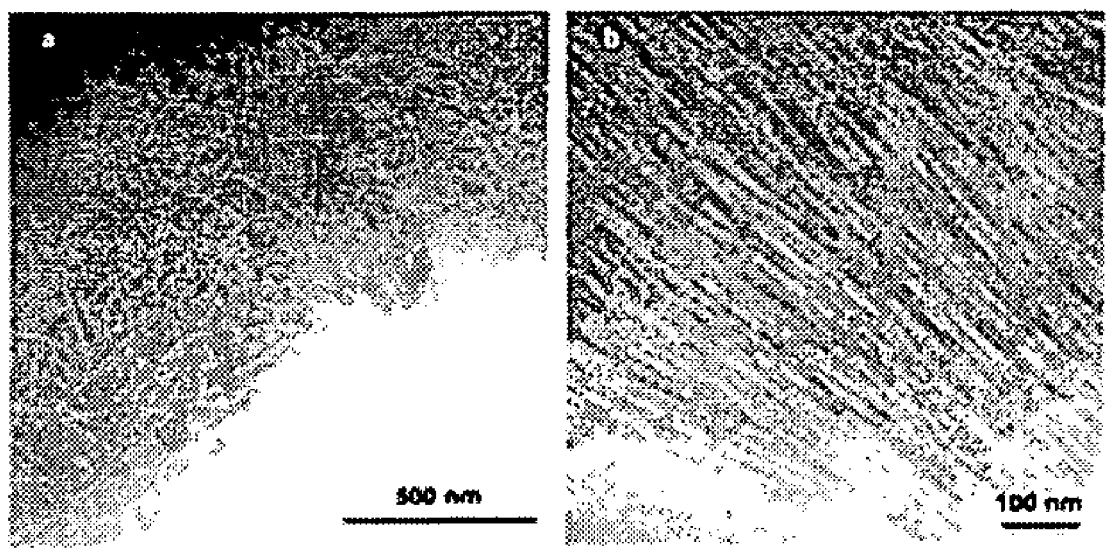
*Figure 22.* TEM images of TMV/silica composites with (*a*) random distribution and (*b*) $Cd^{2+}$ directed parallel alignment of TMV inside silica.

BIONANOMATERIALS AND THEIR SYNTHESIS

PRIORITY INFORMATION

This disclosure claims priority to U.S. Provisional Patent Application Nos. 60/732,279, filed on Nov. 1, 2005, titled "Novel Materials Development by Controllable Virus Assembly" and 60/815,499, filed on Jun. 21, 2006, titled "Synthesis of Functional Nanowires via Virus Assembly," both of which are hereby incorporated by reference in their entirety.

INTRODUCTION

One goal of nanotechnology research is to design and fabricate novel materials with sizes or length scales in the nanometer range. These materials fall into a variety of architectural classes, such as compact clusters, hollow shells, tubes, two-dimensional layers, and three-dimensional molecular networks. In recent years, a wide combination of chemical building blocks and synthetic strategies have been investigated. Numerous specific methods have produced interesting new materials, but a single general strategy for fabricating materials having many different architectures and symmetries has not been developed. Furthermore, most of the recent work has focused on inorganic natural and synthetic materials as building blocks.

More recently, biomaterials (such as bionanoparticles) have been explored as building blocks for nanomaterial development. Bionanoparticles, including, but not limited to, virus and viral like particles, ferritins, and other self-assembled protein cages, are highly ordered nano-scale biological structures generated by nature. For example, viruses are generally composed of genetic material contained within a protective protein shell, sometimes referred to as the capsid. A capsid is composed of proteins encoded by the viral genome and its shape serves as the basis for morphological distinction.

Many viruses can be classified according to their structure as either a rod-like virus or an icosahedral virus. Rod-like viruses appear 1-dimensional on the nanometer scale, but are actually tubular in shape, usually with a hollow center. Most rod-like viruses have helical capsids composed of a single type of protomer stacked around a central circumference to form an enclosed tube resembling a spiral staircase. This arrangement results in rod-shaped virions which can be short and rigid, or long and flexible. Long helical particles must be flexible in order to prevent forces snapping the structure. The genetic material is housed and protected in the inside of the tube. Overall, the length of a helical capsid is related to the length of the nucleic acid contained within it, while the diameter is dependent on the overall length and arrangement of protomers.

One example of a well known rod-like virus is the tobacco mosaic virus (TMV). Each viral particle of TMV has 2130 identical protein subunits arranged in a helical motif around a single stand of RNA to produce a hollow protein tube. The internal and external surfaces of the protein have repeated patterns of charged amino acid residues, such as glutamate, aspartate, arginine, and lysine. The rod-like TMV is about 300 nm long and about 18 nm in diameter. When the RNA and the coat protein of the virus are taken apart, the protein molecules aggregate into a 20S structure under physiological conditions.

TMV is a remarkably stable virion, remaining intact at temperatures up to 60° C. and at pH values between 2 and 10. The known structures of TMV, as well as the ability to reverse engineer this virus, make it a particularly versatile biotemplate for the production of nanocomposites. The highly polar exterior surface of TMV can be used for surface binding and in situ reduction of iron oxyhydroxides, CdS, PbS, gold, nickel, cobalt, silver, iron oxides and silica. Furthermore, genetically modified TMV can improve the metal binding properties.

Icosahedral viruses, on the other hand, have symmetry that results in a spherical appearance of viruses at low magnification, but are actually capsomers arranged in a regular geometrical pattern, similar to a soccer ball, hence they are not truly "spherical". Capsomers are ring shaped structures constructed from five to six copies of protomers. These associate via non-covalent bonding to enclose the viral nucleic acid, though generally less intimately than helical capsids, and may involve one or more protomers.

Two well known examples of icosahedral viruses are cowpea mosaic virus (CPMV) and turnip mosaic virus (TYMV). The diameter of CPMV is around 30 nm. CPMV can be isolated from infected plants in yields of 1-2 g per kg of leaves. It is completely noninfective toward mammals and constitutes no biological hazard. Sixty copies of the two-protein asymmetric unit are assembled in an icosahedral pattern around the single-stranded viral genomic RNA to form the virus particle.

TYMV is one of the best known of the small RNA viruses. It is the type member of the tymovirus group, a nonenveloped plant virus made of a positive single stranded RNA. It shows T=3 icosahedral symmetry and is made of 180 chemically identical protein subunits of 20,000 Da. Large quantities of TYMV can be isolated from infected turnips or Chinese cabbage leafs. TYMV is indefinitely stable from about 4° C. to room temperature, as well as up to about 60° C. for several hours. It is also stable to a wide pH range (4-10) and up to 50% organic solvent. The capsid of TYMV has 32 knob-like structures, and each of these knobs correspond to 20 hexamers and 12 pentamers of the coat protein arranged icosahedrally.

Hierarchical structures of bio-materials have been explored with inorganic linkages between the bio-materials. These inorganic linkages can easily be influenced and weakened depending on the environment of the structure. Also, these inorganically linked bio-materials can have non-uniform size and shape due to the inability to accurately predict bonding between the biomaterial building blocks.

As such, a need currently exists for a hierarchical structure formed from biomaterials having a predictable size and shape. Also, a need currently exists for a hierarchical structure having strong bonding between the biomaterial building blocks.

SUMMARY

Objects and advantages of the invention will be set forth in part in the following description, or may be obvious from the description, or may be learned through practice of the invention.

In one embodiment, the present disclosure is directed to a 1-dimensional composite nanofiber. The composite nanofiber can include a plurality of rod-like viruses defining a head and a tail. The plurality of rod-like viruses can be assembled in a head-to-tail arrangement to form a wire-like structure such that the head of one rod-like virus is adjacent to the tail of an adjacent virus. A polymer can surround the wire-like structure to fix the plurality of rod-like viruses together in the head-to tail arrangement.

For example, the rod-like viruses can include tobacco mosaic viruses. In one embodiment, the rod-like viruses can be functionalized, either before, during, or after assembly in the wire-like structure.

In one embodiment, a composite nanofiber can be made by providing a plurality of rod-like viruses, assembling the rod-like viruses in a head-to-tail arrangement to form a wire-like structure, and polymerizing a plurality of monomers about the wire-like structure. The plurality of rod-like viruses are assembled such that the head of one rod-like virus is adjacent to the tail of an adjacent virus. The polymer can fix the plurality of rod-like viruses together in the head-to tail arrangement.

In another embodiment, the present disclosure is directed to a 2-dimensional nanostructure. The 2-dimensional nanostructure can include a plurality of viruses assembled in a single layer and crosslinked to fix the single layer into the 2-dimensional nanostructure. The plurality of viruses can include rod-like viruses, icosahedral viruses, other shaped viruses, and combinations thereof. In one embodiment, the plurality of viruses can be crosslinked with glutaraldehyde to fix the single layer into the 2-dimensional nanostructure.

A method of forming a 2-dimensional nanostructure can include providing a plurality of viruses, assembling the plurality of viruses into a film-like layer, and crosslinking the plurality of viruses assembled into a film-like layer to fix the 2-dimensional nanostructure.

In yet another embodiment, the present disclosure is directed to a method of making a porous gel. The method can include providing a gel-forming material, dispersing a plurality of viruses into the gel-forming material, and calcinating the gel-forming material. The plurality of viruses can include rod-like viruses, icosahedral viruses, other shaped viruses, other protein assemblies, and combinations thereof. The gel-forming material can be silica-sol gel, other inorganic sol-gels, and other polymeric hydrogels.

Other features and aspects of the present invention are discussed in greater detail below.

BRIEF DESCRIPTION OF THE DRAWINGS

A full and enabling disclosure of the present invention, including the best mode thereof to one skilled in the art, is set forth more particularly in the remainder of the specification, which includes reference to the accompanying figures, in which:

FIG. 5 is the UV-Vis spectra of wt-TMV compared to the UV-Vis spectra of alkyne modified TMV as discussed in Example 1;

FIG. 6 is the MALDI-TOF MS of wt-TMV and alkyne modified TMV as discussed in Example 1;

FIGS. 7a-7d are TEM images of (a) wt-TMV, (b) composite fibers of polyaniline/TMV without negative staining, and (c, d) composite fibers of polyaniline/TMV after negative staining as discussed in Example 1;

FIGS. 8a-8d are AFM height images of (a) wt-TMV, (b) its corresponding phase image, (c) AMF height image of a single composite fibers of polyaniline/TMV, and (d) its corresponding phase image as discussed in Example 1;

FIGS. 9a-9b are (a) UV-Vis spectra of wt-TMV compared to the UV-Vis spectra of composite fibers of polyaniline/TMV and (b) SAXS data of wt-TMV compared to composite fibers of polyaniline/TMV dispersed in a silica gel matrix as discussed in Example 1;

FIG. 10 is a TEM image of polyaniline/PSS/TMV composite nanofibers as discussed in Example 1;

FIGS. 11a-11b are TEM images of PEGMA-326/TMV composite nanofibers as discussed in Example 1;

FIGS. 12a-12b are TEM images of EDOT-$SO_3^-Na^+$/TMV composite nanofibers as discussed in Example 1;

FIGS. 13a-13b are AFH (a) height image and (b) phase image of silica/TMV composite fibers as discussed in Example 1;

FIGS. 14a-14b are TEM images of silica/TMV composite nanofibers as discussed in Example 1;

FIGS. 15a-15d are TEM images of polyaniline/TMV composite nanofibers at a pH of (a) 2.5, (b) 4, (c) 4 and (d) 6 as discussed in Example 1;

FIGS. 16a-16d are TEM image of polyaniline/TMV composite nanofibers at a pH of 4 when prepared with different reaction times of (a) 30 minutes, (b) 1 hour, (c) 2 hours, and (d) 4 hours as discussed in Example 1;

FIG. 17 is a TEM image of emeraline-HCl composite nanofibers synthesized by seeding the reaction using TMV as discussed in Example 1;

FIGS. 18a-18d are confocal fluorescence microscope and SFM images of CPMV assembled stabilized droplets after crosslinking with glutaraldehyde as discussed in Example 2;

FIGS. 19a-19d are TEM images of 2-dimensional nanostructures of (a) a hexagonal array of wt-CPMV, (b) a hexagonal array of wt-TYMV, (c) a square array of wt-CPMV, and (d) the parallel array of wt-TMV as discussed in Example 2;

FIG. 21 is an exemplary porous gel material as discussed in Example 3; and

FIG. 22 is another exemplary porous gel material as discussed in Example 3.

Figure 1:
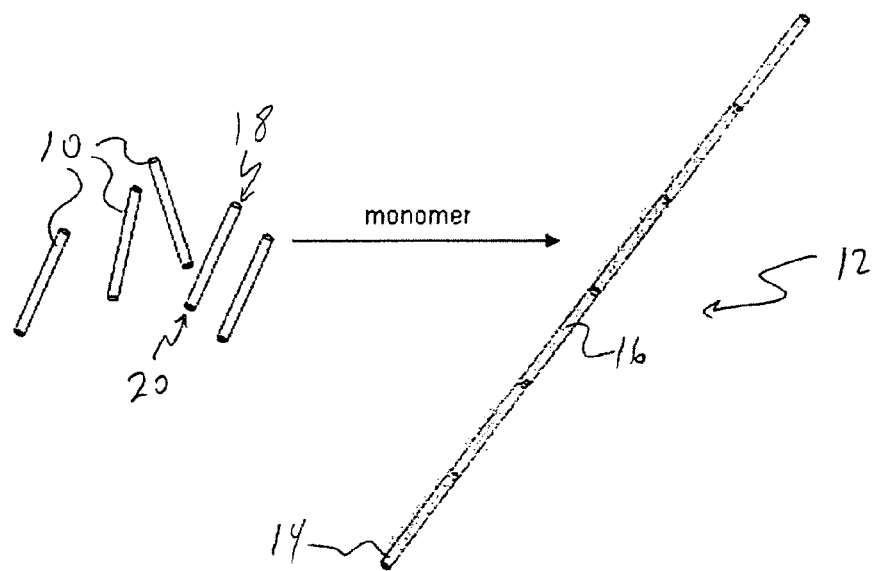
FIG. 1 is an exemplary depiction of a reaction forming a composite nanofiber according to one embodiment of the present invention.

Repeat use of reference characters in the present specification and drawings is intended to represent the same or analogous features or elements of the present invention.

DETAILED DESCRIPTION

Reference now will be made to the embodiments of the invention, one or more examples of which are set forth below. Each example is provided by way of an explanation of the invention, not as a limitation of the invention. In fact, it will be apparent to those skilled in the art that various modifications and variations can be made in the invention without departing from the scope or spirit of the invention. For instance, features illustrated or described as one embodiment can be used on another embodiment to yield still a further embodiment. Thus, it is intended that the present invention cover such modifications and variations as come within the scope of the appended claims and their equivalents. It is to be understood by one of ordinary skill in the art that the present discussion is a description of exemplary embodiments only, and is not intended as limiting the broader aspects of the present invention, which broader aspects are embodied exemplary constructions.

In general, the present invention is directed to, in one embodiment, biomaterials, such as viruses and virus-like materials, used as building blocks for hierarchical nano-structures. Because viruses have known shapes and sizes, viruses are useful as building blocks for hierarchical nano-structures having controlled sizes and shapes. Compared with the inorganic nanoparticles seeding, the uniform shape and size of the viruses can provide highly promising possibilities in self-assembly for the construction of nanoscale materials with hierarchical structure. Also, viruses are susceptible to chemical modification, so one skilled in the art could attach multiple functionalities to the virus, even at specific locations on the virus.

In one embodiment, nanoscale materials as disclosed herein can be functionalized to include one or more predetermined functional chemistries that can provided desired characteristics to a secondary material that incorporates the nanoscale materials. For example, nanoscale materials as described herein can be functionalized so as to preferentially bind a targeted species. The functionalized nanoscale materials can be incorporated in a matrix or otherwise held on a carrier species and be utilized in a separation or concentration regime.

Compared to inorganic or organic nanoparticles, bionanoparticles are truly monodispersed and can be modified in a well defined manner. As such, bionanoparticles are ideal templates and scaffolds for generating nano-based materials with hierarchical structures as they are highly ordered, their detailed structures are known, and they have the ability to be modified both chemically and genetically. For example, a fluorescent functional group can be bonded to a virus, such as disclosed in International Publication No. WO 2005/103705 of Wang, et al., which is incorporated by reference in its entirety.

In another embodiment, nanoscale materials as described herein can be treated so as to bind a second component, e.g., a component describing desired characteristics such as optical characteristics, mechanical characteristics, electronic characteristics, and the like, so as to provide a formed structure incorporating the nanoscale materials with the desired characteristics. For example, an electrically conductive component can be bound to the nanoscale materials either before, during, or following self-assembly of the nanoscale materials and the final product, e.g., a structure incorporating the nanoscale materials can exhibit predetermined electrical characteristics due to the presence of the electrically conductive component on the nanoscale materials.

A. 1-Dimensional Composite Nanofibers

In one embodiment, 1-dimensional nanostructures can be engineered using virus, or virus-like, biomaterials as the building blocks. For example, 1-dimensional nanofibers with high aspect ratios, long lengths, and controllable diameters can be synthesized. Although the present disclosure refers to these structures as 1-dimensional, they are actually 3-dimensional tube-like structures, having a 1-dimensional appearance on the nano-scale.

The fabrication of one-dimensional nanostructures is of considerable interest for advancing nanoelectronics and biomedical applications. By introducing biological elements into the nanomaterials synthesis, it is possible to generate highly ordered and programmable anisotropic structures. For example, a genetically engineered virus can be used to direct the formation of monodisperse single-crystal nanowires with precise control of composition, size and phase.

According to this embodiment, the primary building blocks for these 1-dimensional nanofibers can be rod-like viruses or rod-like virus-like particles. The rod-like virus building blocks can be attached in a "head-to-tail" assembly to form nanofibers having lengths significantly longer than the virus alone. For example, in some embodiments, the nanofibers can have a length of at least about 500 nm (0.5 μm), such as from about 1 μm to about 5 μm. In some embodiments, the nanofibers can have a length of at least about 2 μm, such as at least about 4 μm. In some embodiments, the composite nanofibers can be longer than about 5 μm.

The composite nanofiber, in its simplest form, can be made from a wire-like structure of rod-like viruses positioned head-to-tail and a polymer securing the wire-like structure. For example, under certain conditions the rod-like virus can be made to self-assemble head-to-tail, then a polymer can be polymerized to fix up (e.g., to provide structural integrity holding the rod-like viruses together) the structure, forming long fiber-like composite nanofibers. In one embodiment, a polymerization reaction can polymerize monomers and/or oligomers helically about the self-assembled head-to-tail structure of rod-like virus building blocks.

Figure 2:
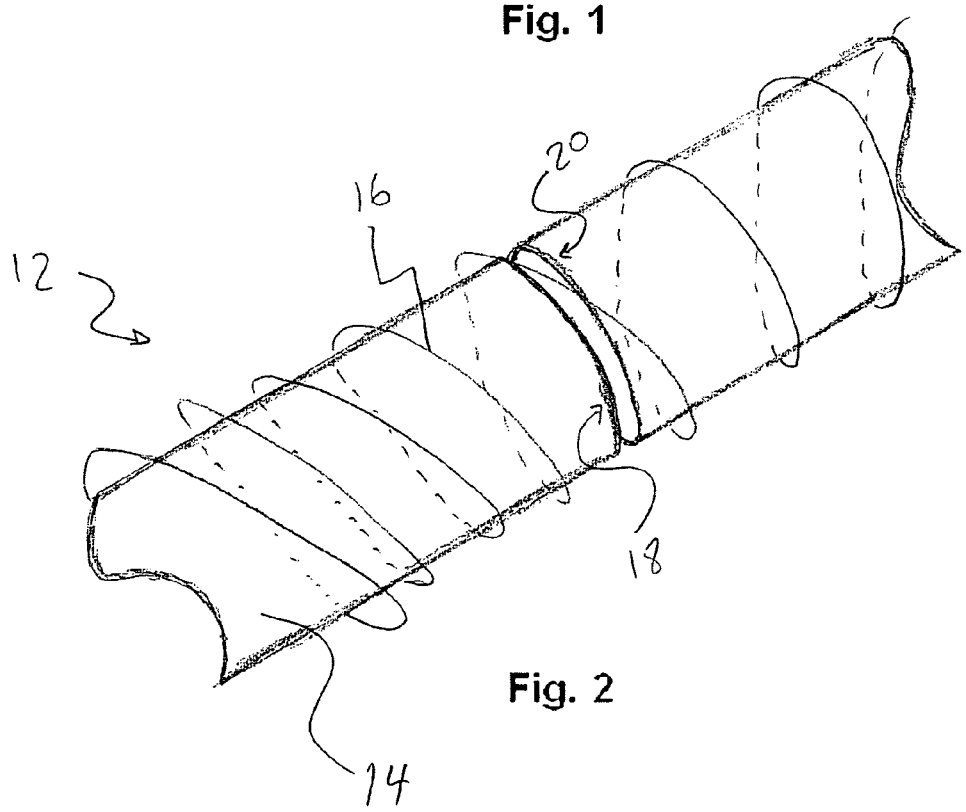
FIG. 2 is a magnification of an exemplary composite nanofiber.

For instance, referring to FIG. 1, the rod-like virus particles 10 self-assemble head-to-tail into a continuous wire-like structure. The rod-like virus particles 10 have heads 18 and tails 20. Then, the self-assembled wire-like structure can be fixed by polymerization of a monomer about the wire-like structure. As such, a composite nanofiber 12 is formed of wire-like structure 14 of the self-assembled virus particles 10 fixed together with polymer 16 wrapped about the wire-like structure 14. FIG. 2 is a magnification of an exemplary composite nanofiber 12 showing the head 18 of one rod-like virus particle 10 assembled adjacent to the tail 20 of an adjacent rod-like virus particle 10 to form a wire-like structure 14. Polymer 16 is wrapped about the wire-like structure 14 to fix the head-to-tail assembly of the rod-like viruses.

Any rod-like virus that can be assembled head-to-tail can be used to form the wire-like structure of the composite nanofiber, including, but not limited to, rod-like bacteriophages (e.g., fd phage, M13 phage, 1IFD phage), potato X potexvirus, and the like. In one particular embodiment, when tobacco mosaic virus (TMV) particles can be used as the building blocks of the wire-like structure. For instance, a head-to-tail ordered self-assembly of wild type TMV (wt-TMV) can naturally occur, likely a product of complementary hydrophobic interactions between the dipolar ends of the helical structure. In an acidic environment, this 1-dimensional self-assembly is dramatically favored by minimizing the repulsion between the carboxylic residues at the assembly interface.

When a wire-like structure is formed from tobacco mosaic virus (TMV) particles, and without wishing to be bound by theory, it is believed that monomers with amino groups can accumulate on the surface of TMV due to the hydrogen bonding or the electrostatic attraction between the negative-charged TMV and the positive-charged ammonium group of the monomer at a pH above the isoelectric point of TMV (around 3.2). Therefore, the in situ polymerization can produce a thin layer of polymers on the surface of TMV, and fix the head-to-tail assembled wire-like structure. For instance, in one embodiment, aniline can be a suitable monomer, due to the ease of polymerization and the intrinsic anisotropic morphology that polyaniline possesses. In such situations, other weaker interactions, including without exception charge-charge attraction, hydrophobic interaction, H-bonding, and pi-pi stacking interaction can play a role to attract the monomers on the surface of the rod-like viral particles. In addition, any other suitable monomer, or combination of monomers, can be used to fix the wire-like structure of virus particles following self-assembly. However, other suitable polymers may be formed from positively charged monomers, such as amino or thiol groups, to fix the wire-like structure, including, but not limited to, polypyrole, polythiophene, polyethylenedioxythiophene, polypyrazole, and derivatives and copolymers thereof. Alternatively, other polymerization techniques can be used to fix the wire-like structure, including, but not limited to, radical polymerization of olefins (e.g., polyethylene, polypropylene, etc,), enzyme catalyzed polymerization, polymerization of aryl compounds with electrical chemistry, and ring opening metathesis of cycloalkene monomers.

According to one embodiment, the rod-like virus particles can be modified, as known in the art, which can add a desired functionality to the resulting composite nanofiber. For instance, conductive, magnetic, and other functional materials can be introduced either on the exterior or interior surface of the rod-like virus particles of the composite nanofiber. The rod-like virus particles can be modified before, during, or after the formation of the composite nanofiber. A composite nanofiber can be treated to as to include a variety of functional groups, including, without limitation, conductive polymers, fluorescent materials, cell-binding motifs, inorganic metal oxide, metals, etc. As such, the disclosed processes can offer a versatile way to fabricate functional 1-dimensional nanostructures with high aspect ratios. In addition, the processibility can be very good compared to other reported synthetic 1-dimensional materials.

B. 2-Dimensional Nanostructures

In another embodiment, 2-dimensional nanostructures, such as films and webs, can be engineered using virus, or virus-like, biomaterials as the building blocks. Although the present disclosure refers to these structures as 2-dimensional, they are actually 3-dimensional structures, having a 2-dimensional appearance on the nano-scale.

According to this embodiment, the primary building blocks for these 2-dimensional nanostructures are virus, or virus-like, biomaterials of any shape, including, without limitation, rod-like and icosahedral. According to one embodiment, the virus biomaterials can be arranged in a single layer to form a 2-dimensional nanostructure. The 2-dimensional nanostructure can then be crosslinked to fix the 2-dimensional shape.

A two-dimensional film such as may be formed including a plurality of cross-linked biomaterials can be functionalized to include a desired chemistry. Following which, a film can provide a large surface area for applications such as separation protocols, concentration protocols, filtration protocols, and the like. For instance, following adsorption of a target analyte to the film, the analyte can be recovered via elution with any suitable, compatible solution to which the analyte has a higher affinity as compared to the film surface. For example, a species may be held to the film surface with a disulfide bond. During a concentration protocol, the disulfide bond may be broken in the presence of a reducing agent. For instance, a reducing agent such as mercaptoethanol can be caused to flow on to the film surface, and the disulfide bonds can be broken. The targeted species can thus be removed from the film in a concentrated and/or purified solution, and the functional chemistry can remain on the substrate surface to be utilized again. Concentration of species can greatly improve sensitivity of detection of the species, for instance via mass spectrometry methods including electrospray ionization (ESI-MS) methods and matrix-assisted laser desorption-ionization (MALDI) methods.

A two-dimensional film as described herein can be further derivatized with additional materials such as conductive materials or materials including particular optic characteristics to provide a film describing desired characteristics, e.g., conductivity, optical polarity, and the like.

In another embodiment, a two dimensional film can be utilized as formed, without additional functionalization. For example, the film can include porosity as formed, and can be utilized in a microfiltration protocol. In another embodiment, the biomaterials and/or the cross-linking moities can describe a predetermined hydrophobicity or other surface characteristics, and the film can be utilized to provide a controlled flow pattern on a nano- or micro-scale.

A two-dimensional film can be combined with additional materials. For instance a film can be combined with additional layers to provide a multilayer film, as a laminate, for example, including one or more layers of the biomaterial film. Thus, the biomaterial-based film can provide mechanical, electrical, optical, chemical, or any other desired characteristics to the multilayer film via characteristics of the biomaterials utilized in the film, the cross-linking materials, additional components included in the film, one or more functional chemistries added to components of the film, and the like.

The virus biomaterials can be arranged in a single layer to form a 2-dimensional film-like layer according to any method. For example, the virus biomaterials can self-assemble into a thin, film-like layer at a liquid-liquid interface between immiscible liquids, or at an interface between a mixture of phases, e.g., at a liquid-gas interface, at a solid-liquid, or at a solid-gas interface. In one embodiment, biomaterials can be co-assembled with diblock compolyers to form a two-dimensional thin film arrangement.

In one particular embodiment, virus biomaterials can self assemble at the interface between immiscible liquids, such as oil and water, to form a thin, 2D film of virus biomaterials. The interface between immiscible liquids can offer control of the hierarchical self-assembly of the virus biomaterials due to the weak enthalpic driving force of the viruses at the interface. Also, the ability to precisely tune the interface interactions and the truly monodisperse nature of the virus biomaterials can offer the ability to control the hierarchical self-assembly of the virus biomaterials into a 2-dimensional film. Additionally, by manipulating ligands attached to the virus biomaterials (either naturally occurring ligands or added ligands), the dynamic nature of the assemblies and the formation of robust structures via interface chemistries can be precisely controlled. For instance, functional groups can be added to the outer surface of the virus biomaterials in order to facilitate their self-assembly at the liquid-liquid interface.

Once the virus biomaterials are assembled into a 2-dimensional layer, the virus biomaterials can be crosslinked to fix the 2-dimensional nanostructure. In one particular embodiment, the virus biomaterials can be crosslinked at free amines on their outer surface with glutaraldehyde. Thus, this glutaraldehyde crosslinking can fix the self-assembled 2-dimensional film-like layer of virus biomaterials into a 2-dimensional nanostructure. Surprisingly, it has been found that glutaraldehyde crosslinking does not disrupt the integrity of virus biomaterials.

Alternatively, other crosslinking methods can be utilized to fix a self-assembled 2-dimensional film-like layer of virus biomaterials into a 2-dimensional nanostructure, including, but not limited to, crosslinking mannose or glucose ligands with concanavalin A (or other sugar-lectin binding), crosslinking metal ligands with other metals, crosslinking biotin ligands avidin/streptavidin, crosslinking azide or alkynes to form triazole linkages, and the like. In other embodiments, particular amino acids of a capsid can be targeted for a crosslinking agent. For example, the thiol groups (of cysteines), the carboxyl groups (of aspartic acid and glutamic acid), and the phenol groups of tyrosines can be crosslinked, according to methods known in the art. In another embodiment, photoinitiated crosslinkers can be used e.g., acrylates and the like, as are generally known in the art.

Any virus biomaterial can be used as the building blocks of the crosslinked 2-dimensional nanostructure. In one particular embodiment, the virus biomaterial is selected from the groups of rod-like viruses or icosahedral viruses. Also, in one embodiment, a combination of different types of viruses can be used to form a crosslinked 2-dimensional nanostructure.

Figure 3:
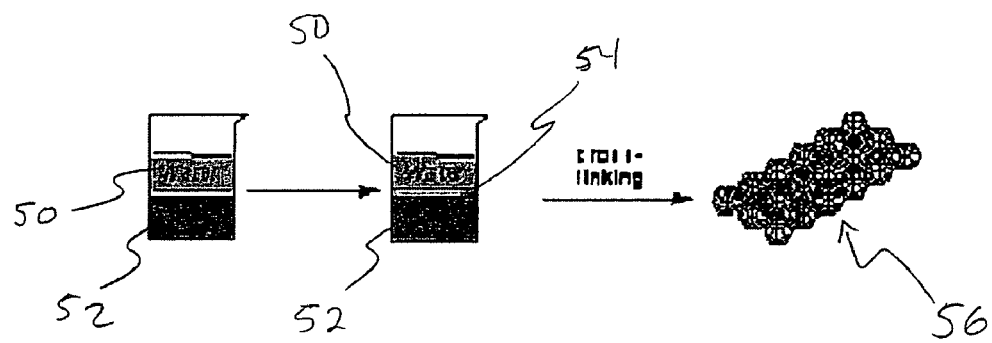
FIG. 3 is a depiction of an exemplary method of forming a 2-dimensional nanostructure according to one embodiment of the present invention.

For example, as shown in FIG. 3, the interface 54 of water 50 and oil 52 can be utilized to promote formation of a crosslinked 2-dimensional nanostructure. For example, the virus biomaterial can be suspending within one phase, e.g., the water 50. Following which, oil 52 can be added to the water/virus suspension 50. The mixture can then be allowed to separate. At the water/oil interface 54, the virus biomaterials can self0assemble to form a 2-dimensional film-like layer. The 2-dimensional film-like layer of virus biomaterials can then be crosslinked to form a crosslinked 2-dimensional nanostructure 54 having a substantially planar shape.

Figure 4:
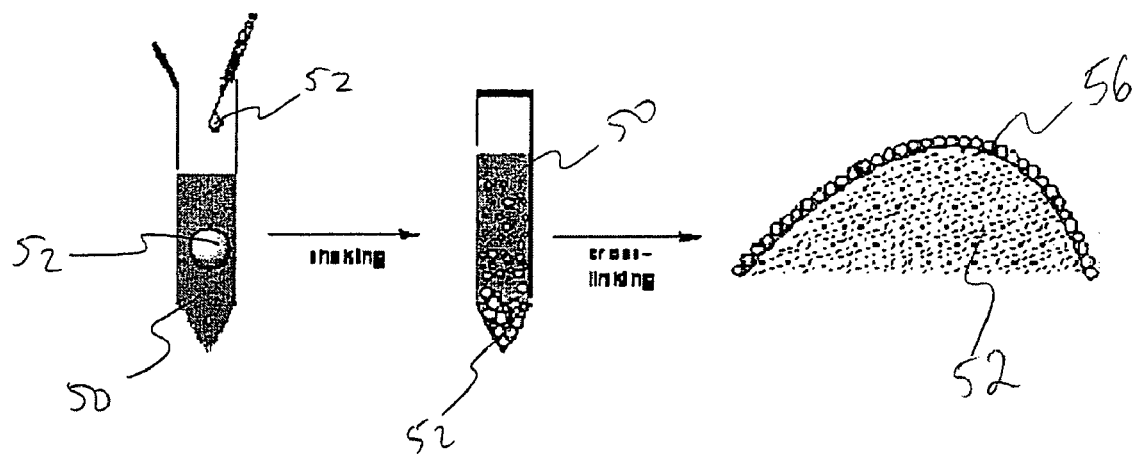
FIG. 4 is a depiction of another exemplary method of forming a 2-dimensional nanostructure according to one embodiment of the present invention.
Figure 20:
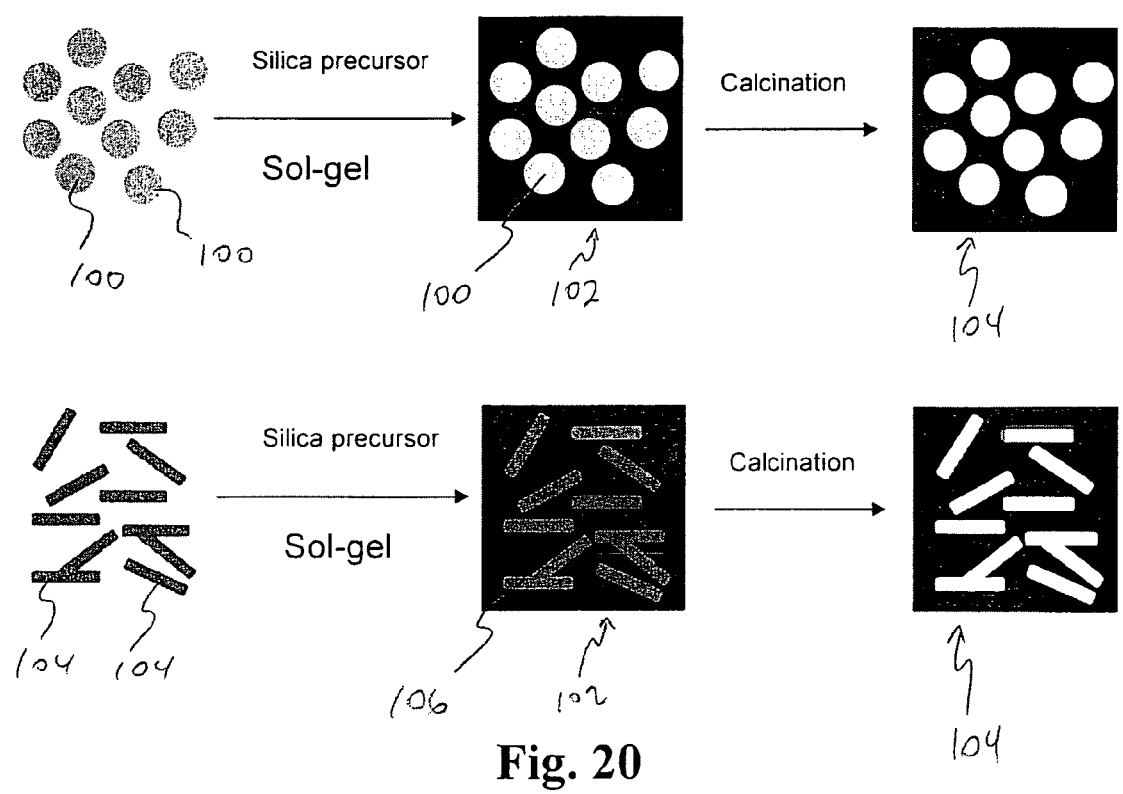
FIG. 20 is an exemplary method of forming a porous gel material.

Alternatively, as shown in FIG. 4, oil droplets 52 can be added to water 50 containing the virus biomaterials in suspension. Then, the mixture can be agitated to disperse the suspended biomaterials within and among the oil droplets prior to agglomeration of the oil droplets within the suspension. Upon this dispersion, a 2-dimensional film-like layer of virus biomaterials can self-assemble about each of the oil droplets. Following this initial formation of the films, crosslinking can be initiated within the suspension through, e.g., addition of a crosslinking agent to the suspension or activation of a crosslinking agent previously included in the suspension (e.g., photoinitiation) and the 2-dimensional film-like layer of virus biomaterials encircling each oil droplet can be crosslinked to form a suspension including droplets of oil 52 surrounded by a crosslinked 2-dimensional nanostructure 54. In another embodiment, the phases can be reversed, e.g., droplets of water including suspended biomaterials therein can be added to a carrier oil phase. Following initiation of a crosslinking agent, an oil suspension including therein a plurality of water droplets surrounded by a crosslinked 2-dimensional nanostructure can be formed.

Although water and oil can be used as the immiscible liquids, this is not a requirement of the disclosed subject matter and any other immiscible liquid combinations could be used. For instance, in an alternative embodiment, a perfluorodecalin/water interface could be used to form the 2-dimensional film-like layer of virus biomaterials.

Similar to the 1-dimensional composite nanofiber rod-like virus particles, described above the virus biomaterials crosslinked to form the 2-dimensional nanostructure can be modified, as known in the art, which can add a desired functionality to the resulting 2-dimensional nanostructure. For instance, conductive, magnetic, and other functional materials can be easily introduced either on the exterior or interior surface of the virus particles of the 2-dimensional nanostructure. The virus particles can be modified before, during, or after the formation of the 2-dimensional nanostructure. Additionally, such a 2-dimensional nanostructure can be coated with a variety of functional groups, including conductive polymers, fluorescent materials, cell-binding motifs, inorganic metal oxide, metals, etc. As such, the 2-dimensional nanostructure can be effectively used as in filtration, as a scaffold for reactions (catalysis), a scaffold for inducing cell bonding, etc.

Moreover, as a film as described herein can be shaped as desired, a film can be utilized in any predetermined geometric shape. For instance, a film can be functionalized to preferentially bind a targeted species, such as a targeted surface receptor on a cell. In addition, the film can be shaped to a desired geometric configuration. Following initial bonding of living cells to the surface of the film, the cells can be encourage to grow and develop at the surface held in the predetermined configuration. As such, the disclosed biomaterial films can be beneficially utilized in tissue engineering applications to provide a synthetic tissue in a predetermined geometric configuration.

For example, CPMV can provide a robust platform for PEG chains, biotin, DNA, peptides, antibodies and carbohydrates. This strategy permits the covalent installation of functional groups in multiples of 60 at well-defined locations. Furthermore, it can be manipulated at the genetic level to introduce mutations at desired positions. Thus, in one particular embodiment, modified CPMV can be assembled into a film-like layer and crosslinked to form a 2-dimensional nanostructure having desired functionalities at specific locations.

C. Co-Assembly of Virus Nanoparticles with Silica Precursor

In another embodiment, viruses and virus-like biomaterials can be used with an inorganic sol-gel process to generate nanocomposite materials. As shown in FIG. 20, virus nanoparticles can be used as the template to synthesis viruses/silica composite materials and related porous materials after removing the viruses and virus-like biomaterials.

Any gel forming substance can be used in accordance with this embodiment, including but not limited to silica gels (e.g., silica-sol gels) or any other hydrogel.

For example, referring to FIG. 20, an exemplary process is shown, using differently shaped virus particles. First, icosahedral viruses 100 can be dispersed into silica sol-gel, by slow addition and stirring to form a silica-sol gel dispersion 102 containing dispersed icosahedral viruses 100. Then, the silica-sol gel dispersion 102 can be calcinated to form the porous silica-sol gel 104.

Alternatively, or in addition to, the icosahedral viruses 100, rod-like viruses 104 can be used, along with any other shaped virus. As such, the pore size of the resulting porous silica-sol gel can be controlled based on the selection of the virus(es). For example, the porous silica-sol gel can be a mesoporous gel having pores in the range 2-50 nm in diameter, such as 2-20 nm in diameter.

In some embodiments, the arrangement of the virus particles can be controlled. For instance, in one embodiment, divalent metals, such as $Cd^{2+}$ or $Zn^{2+}$ or $Ca^{2+}$, can align the organization of rod-like viruses in the gel.

Example 1

Composite Nanofibers

Wild-type tobacco mosaic virus (wt-TMV) was combined with aniline polymerization to generate composite nanofibers. The TMV can self-assembly according to the head to tail under certain conditions, then polyaniline was polymerized about the self assembled wt-TMV to fix up the structure to form long fiber-like composites. When the wt-TMV was used as templates, the resulting composite nanofiber had an average length of about 4 μm and the diameter was around 25 nm. When the reaction conditions were changed, a longer fiber could be obtained as shown both by TEM and AFM results, which showed the length of fiber to be as long as more than 10 μm.

o-Toluenesulfonic acid modified TMV (m-TMV), as modified as shown in the reaction scheme shown below, was also used to form composite nanofibers:

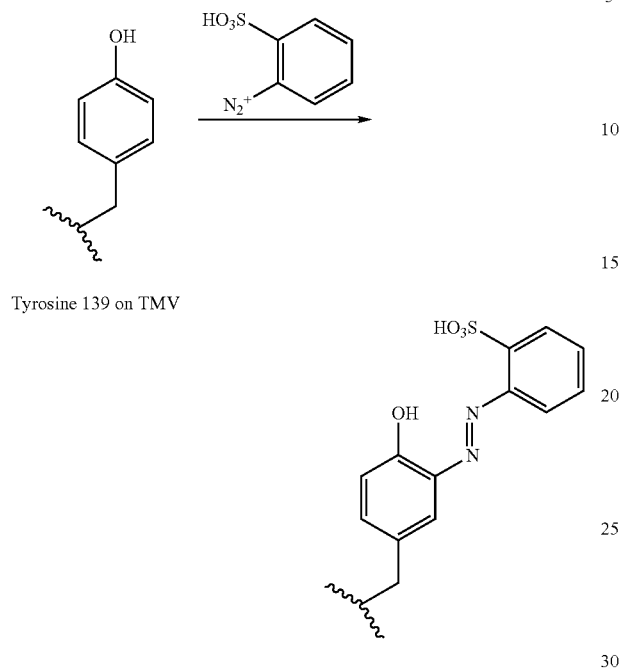

Tyrosine 139 on TMV

This modification changed the surface charge property of wt-TMV by the acid modification (o-toluenesulfonic acid). The stability of wt-TMV in aqueous was determined by the salt concentration, pH values, temperature and the surface change of TMV, so this modification method was a relatively simple way to get a more stable TMV solutions in a wide pH values range. The difference of the surface charge of the TMV would have an influence on the binding of metals, semiconductor, and other materials on the surface of the TMV as well as on the self-assembly properties of the TMV. As shown in table 1, for the wt-TMV, the zeta potential is −21.47 at the pH 7.94. However, for the o-toluenesulfonic acid modified TMV (m-TMV), the zeta potential is −45.20 at pH 8.01. The charges for the m-TMV were changed two times compared with the wt-TMV. Even at pH 4.54, the surface charge of m-TMV was larger than the wt-TMV at pH 7.94. With reference to the date shown in Table 1, the isoelectric point of wt-TMV was found to be a little greater than 3.39, which is similar to values found in the literature. For the m-TMV, the isoelectric point was found to be below 3.27.

TABLE 1

| | pH | Zeta potential |
|---|---|---|
| wt-TMV | 7.94 | −21.47 mv |
| wt-TMV | 2.39 | 29.20 mv |
| wt-TMV | 3.39 | 4.58 mv |
| m-TMV | 8.01 | −45.20 mv |
| m-TMV | 4.54 | −25.61 mv |
| m-TMV | 3.27 | −0.19 mv |

The m-TMV formed 1-dimensional composite nanofibers according to the reaction shown in FIG. 6. The diameter of the formed composite fiber is around 25 nm and the length of composite fiber is as long as 2 μm.

Alternative Chemical Modification of TMV

Alkyne functionality was attached to the exterior capsid of TMV using a diazo linkage. An ethynyl group was placed at the meta- and para-positions of an analine and followed with the below reaction Scheme 1 to attach this small molecule to available tyrosine residues:

Scheme 1

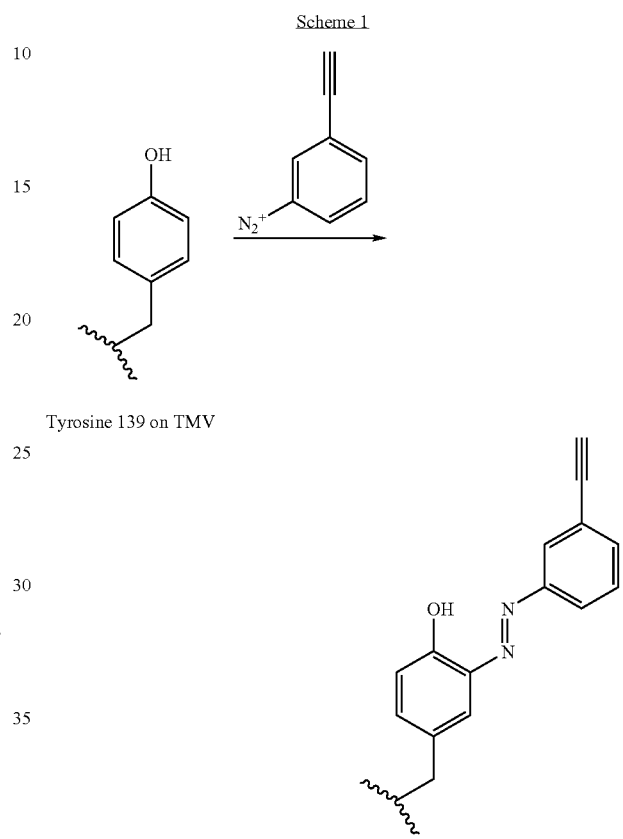

Tyrosine 139 on TMV

This alkyne functionality was met with an azide to form a 1,2,3-triazole ring via a copper catalyzed cycloaddition. The synthesis of this modified TMV worked very well and was confirmed by UV-Vis (FIG. 5), MALDI-TOF MS (FIG. 6) and through visual confirmation through the change of color of the solution. It was previously reported that only tyrosine 139 was being modified on the protein subunit. In this work, a significant number of protein subunits were modified with two and three of these small molecules. This was confirmed by subsequent peaks seen using MALDI-MS data of the full protein subunit (FIG. 3). The reason for these additional modifications may be due in part to the modification of the protein subunits located at the ends of the viral particle. Other groups that were attached to the tyrosine residue of TMV were sulfanilic acid, p-aminobenzoic acid, 2,5-disulfoanaline and 5-aminoisophthalic acid.

Preparation of 1D Polyaniline/TMV Composite Fiber

The TMV head-to-tail assembly was confirmed by transmission electron microscopy (TEM). Upon staining with uranium acetate, native TMV appeared as rod-like particles with an average diameter of 18 nm (FIG. 7a). Besides a small percentage of broken particles that were shorter than 300 nm, most of the particles were 300 nm long, which was consistent with the prior literature. Without negative staining, the long fiber structure was clearly shown after deposited on carbon-coated copper grids (FIG. 7b). In contrast to native TMV, the length of the fiber can be as long as 10 µm based on the TEM observations (FIGS. 7b and 7c). As shown in FIG. 7d, the composite nanofibers were monodispersed in width with an average diameter of ~21 nm. Due to the near neutral polymerization condition, polyaniline formed with this method is in the insulating form, which shows a yellowish color in solution.

Atomic force microscopy (AFM) was also used to characterize native TMV and composite fibers. The samples were directly dropped on the silicon wafer and dried at ambient conditions. The average length of native TMV is around 300 nm as shown in FIGS. 8a and 8b. The small round dots displayed in the images could be a 20S structure of TMV formed by reversible dissociation or mechanic damage of native TMV. FIGS. 5c and 5d show a single 1D assembled TMV/polyaniline composite fiber. It was about 1.6 µm long with a very smooth surface without any visible gap. The head-to-tail protein-protein interaction thus was found to lead to the formation of the fiber-like structures. Such interaction, in principle, is identical to the subunits' interaction at any cross-section of the native TMV structure. The surface polymerization of aniline together with the attractive interaction between polyaniline and TMV further stabilizes the resulting composited fibers, and compensates the entropy-loss of the assembly process.

The formation of polyaniline was confirmed by UV-vis absorption studies. Thorough dialysis against deionized water gave a polyaniline/TMV composite sample which showed two absorption peaks at 260 nm and 427 nm (FIG. 6a). The peak at 260 nm was attributed to the absorbance of TMV, and the peak at 427 nm was attributed to the polyaniline in a branched form.[13] Small angle X-ray scattering (SAXS) was used to measure the increase in the diameter of TMV quantitatively upon surface polymerization. Interestingly, TMV and polyaniline/TMV composite fibers showed similar scattering data in water (data not shown), probably because the average electron density of the polymer layer is similar to that of water.

Fibers were embedded into a silica gel matrix. The scattering was then mainly due to the silica volumes that were excluded by the fibers (FIG. 6b) and was sensitive to the overall diameter of the fibers. The form factor of rod-like particles depended on both the length and the diameter of the particle. Since the length of the fibers were much greater than the diameter, the position of the first minimum in the scattering curve corresponded to the first zero of Bessel function $J_1(qR)$. The diameter of native TMV was found to be 16.7 nm, and that of the composite fiber was 17.7 nm. Although this value is slightly lower than the TEM result, it is consistent with a surface coating of the TMV with polyaniline.

A very interesting feature of the present synthesis was that the polymerization of aniline took place only on the surface of TMV. Scanning force microscopy (SFM) was used to analyze the reaction mixture before purification. The reaction solution was directly diluted 10 times with pure water and spin-coated on silicon wafer. Both height and phase images showed that the length of composite fiber to be longer than 20 µm. It was difficult, though, to determine the exact diameter for the soft protein samples. However, no bulk polyaniline or pure polyaniline nanofibers were formed in the reaction. Without TMV as a template, highly aggregated polyaniline with a small amount of nanofibrillar polymers were produced, which is consistent with prior results.

Preparation of polyaniline/TMV Bundle

It was interesting to investigate the composite structure when the pH values were changed to get conducting polyaniline/TMV composites. As shown in FIG. 7a, at pH 2.5, small polyaniline fibers were obtained. No intact TMV could be found after 24 hours reaction. TMV cannot remain intact at low pH values and low ionic strength for a long time. With pH increases to 5, a bundled structure was clearly seen, as shown in FIG. 7b. The length of the bundle was around several micrometers, while the width of bundle was around 1-2 micrometers. An enlarged image clearly shows TMVs/fibers were arranged parallel to form a bundled structure (FIG. 7c). The similar bundled structures were obtained at pH 4 and 5.5. When the pH was increased to 6, one dimensional long composite fibers were formed (FIG. 7d).

There were two possible theories considered as to how the bundled structure were formed as shown in FIG. 7b and FIG. 7c. One possible reason was that at low pH, and due to the weakly charged surface of TMV, TMVs were easy to form side by side assembly. When aniline and oxidant were added into the solution, the polymerization of aniline fixed the bundle structure. The other possibility was that whether at low or high pH, TMVs were first formed head-to-tail. With continued reaction of aniline, the surface charge of TMV/polyaniline fibers would be reduced with more polyaniline accumulated on the surface of TMV, and the bundled structure would then be formed.

A series of experiments were designed to determine which possibility was more likely. As shown in FIG. 8a, after 30 minutes the reaction solution was placed on the TEM grid to check morphology, no bundled structure was found. Most of the TMVs formed short fibers due to TMV head-to-tail assembly. Both long fibers and side by side assembled fiber structures were found when the TEM was checked after 1 h (FIG. 8b and FIG. 8c). When the reaction time was longer than 4 h, no single fiber could be found. All the fibers accumulated together to form the bundled structure (FIG. 8d).

TMVs as Seeds to Prepare Polyaniline Nanofibers

Polyaniline is a conducting polymer that has been widely studied for electronic and optical applications. Synthesis of polyaniline 1-D nanostructures has been carried out both chemically and electrochemically by polymerizing the monomer either with the aid of a template or at the oil-water interface. Compared with the inorganic nanoparticles seeding, the uniform shape and size of the rod-like TMV provides highly promising possibilities in self-assembly study for the construction of nanoscale materials with hierarchical structure. Here is presented another facile method to prepare polyaniline nanowires by using TMV seeding process. It is important to note that just ~0.2 mg of the seed TMVs was sufficient to change the morphology of the bulk precipitate 20 mg quantitatively to nanofibers. The TEM image of the polyaniline obtained in the TMV seeded experiment show fibrillar morphology with fibers having an average diameter in the range 30-40 nm (FIG. 9). Four probe pressed-pellet conductivities for polyaniline nanofibers were in the range 4-20 S/cm, similar to conventional emeraldine-HCl powder.

Preparation of Poly(Sulfonated Styrene)/Polyaniline/TMV Composite Nanorods

Due to the weakly charged surface of TMV and the polymerization of aniline further reducing the charge of polyaniline/TMV composite fibers, a conductive bundled structure was formed. It was difficult to get single conductive polyaniline/TMV composite fiber. However, by using poly(sulfonated styrene) (PSS) as a stabilizer agent and as co-doping agents, single polyaniline/PSS/TMV conductive nanofibers could be obtained. As shown in FIG. 10, the native TMV was 18 nm in diameter, the diameter of the composite fiber in comparison was 25 nm. Unlike most of the solution synthesis methods for polyaniline nanofibers that can only produce interconnected, branched networks, the polyaniline/TMV composite nanowires synthesized by this method were predominantly isolated single fibers that could be perfectly dispersed in a dilute solution, or easily dispersed on solid surfaces by simple spin-coating or dip-coating. A transparent blue-color thin film was formed after drying at room temperature for 24 hrs. Four probe conductivity for polyaniline nanofiber thin film was in the range of 0.01-0.1 S/cm.

Preparation of TMV/PEGMA-326 Composite

The TEM image of TMV/PEGMA-326 of FIG. 11 prepared at pH 5.22 showed a lot of bundle composite with a size of about 2 micron wide and about 10 microns long. The overall trend for these assemblies was that the composite morphology changed from bundle to fiber to TMV when pH went up. At pH 6.37, some long fibers about 3 microns were observed.

Preparation of TMV/EDOT-SO$_3^-$Na$^+$ Composite

The TEM image of TMV/EDOT-SO3-Na$^+$ of FIG. 12 prepared at pH 7.3 for 24 h showed a lot of fiber about 4 microns long. At 74 h, TEM image showed no fibers but only bundles. Their sizes were about 14 microns long and 0.8 micron wide. The general trend was that the composite morphology changed from TMV to fiber to bundle with time.

Preparation of Silica/TMV Composite Fiber

The surface chemistry of TMV coupled with the unusual high stability of the protein assembly provided a structured substrate for the site-specific nucleation of a variety of inorganic solids at a range of pH values and reaction conditions. In the case of silica mineralization, either at low pH or high pH, silica/TMV nanotubular superstructure could be formed. However, it was difficult to control the assembly structure into a homogenous one dimensional long fiber.

When ammonium phosphate monobasic was used as an assisted agent, in an acidic condition, homogeneous silica/TMV composite long fibers were readily obtained. As shown in FIG. 13, both height and phase image images showed that the length of composite fiber could be longer than several microns. It was difficult, though, to determine the exact diameter for the soft protein samples. However, no bulk silica was formed in the reaction. TEM studies gave the similar result. As shown in FIG. 14, the length of the composite fiber was found to reach several microns. The composite nanofibers are monodisperse in width with an average diameter of ~21 nm.

The following is a description of the general procedures for the experiment described herein:

Purification

Tobacco plants approximately 1 month old were inoculated with wt-TMV. The leaves were harvested and the virus was isolated from the host plant. Briefly, the leaves were crushed and blended with 0.01 M K-phosphate buffer at pH 7.8 with 0.2% ☐-mercaptoethanol. The mixture was centrifuged at 9000 rpm for 15 minutes after which the supernatant was clarified with 1:1 CHCl$_3$:1-butanol. The aqueous portion was separated by centrifugation and TMV was precipitated by the addition of PEG 8K to 10% and NaCl to 0.2M. The resulting pellet was resuspended in 0.01 M K-phosphate buffer at pH 7.8. After a final round of ultracentrifugation at 42 k rpm for 2.5 h, the resulting pellet was resuspended overnight in 0.01 M K-phosphate buffer at pH 7.8 or in pure water. For the purification of TYMV and CPMV, the procedure was similar with that TMV.

Modification of TMV

Diazonium salts were synthesized by mixing 200 μl 160 mg/ml aqueous o-toluenesulfonic acid monohydrate, 200 μl 32 mg/ml aqueous sodium nitrite and 1.04 ml 10 mg/ml 4-aminobenzoic acid at 0° C. for 1 hr. 2 ml of a 15 mg/ml stock solution of TMV in 0.01 M phosphate buffer was diluted with 5.2 ml 150 mM aqueous borate buffer. To this solution was added 1440 μl of the diazonium salt solution prepared above. The reaction mixture was placed in an ice/water box in a 4° C. for 2 h, after which the solution was a deep yellow color. Ultracentrifugation at 42000 rpm for 2.5 h afforded a brown pellet, which was resuspended overnight in 10 mM pH 7.8 phosphate buffers at 4° C.

Preparation of Polyaniline/TMV Composite Nanofibers

Before polymerization, aniline was first distilled at reduced pressure. In a typical experiment, distilled aniline (10 μL) was introduced into a 1 mg/mL pH 5.5 solution of TMV in pure water (5 mL), followed by addition of ammonium persulfate (10 mg). The final pH values of the reaction solution were around 6.5. The reaction mixture was incubated at room temperature for 24 hours to form a yellow suspension. After centrifugation at 8'000 g for 3 min, the pellet was quickly rinsed for three times with pure water, and resuspended in deionized water to afford the pure polyaniline/TMV composite.

Preparation of Poly(Thiophene Salt)/TMV Composite

In a typical experiment, thiophene salt (10 mg) was introduced into a 1 mg/mL pH 5.5 solution of TMV in pure water (5 mL), followed by addition of ammonium persulfate (10 mg). 0.1 M HCl was used to adjust pH values. After centrifugation at 8'000 g for 3 min, the pellet was quickly rinsed for three times with pure water, and resuspended in deionized water to afford the pure poly(thiophene salt)/TMV composite.

Preparation of Silica/TMV Composite Nanofibers

In a typical experiment, tetraethyl orthosilicate(TEOS) was diluted 10 times by ethanol. 40 μL diluted TEOS solution was introduced into a 1 mg/mL pH 3.8 solution of TMV in 2 mg/mL ammonium monophosphate solution (5 mL). After centrifugation at 8'000 g for 3 min, the pellet was quickly rinsed for three times with pure water, and resuspended in deionized water to afford the pure silica/TMV composite.

Preparation of Poly(Sulfonated Styrene)/polyaniline/TMV Composite Rods

In a typical experiment, distilled aniline (10 μL) was introduced into a 1 mg/mL pH 5.5 solution of TMV in pure water (5 mL), followed by addition of 30% poly(sulfonated styrene) (PSS) (67 μL). After stirred for 10 minutes, ammonium persulfate (10 mg) was then introduced. 0.1M HCl and 0.1M NaOH solution were used to adjust pH values. After centrifugation at 8'000 g for 3 min, the pellet was quickly rinsed for three times with pure water, and resuspended in deionized water to afford the pure PSS/polyaniline/TMV composite.

Preparation of TMV/PEGMA-326 Composite

TMV (1 mg), PEGMA-326 (100 uL, 20 mg/mL), and ammonium persulfate solution (127 uL, 10 mg/mL) were added to a small vial equipped with a stirring bar. Nanopure H2O (~630 uL) was added to make the mixture volume to about 1 mL and stirred. The mixtures were adjusted to a series of pH ranging from 5.22 to 9.02 by the diluted HCl and NaOH solution. The reaction vials were capped and stirred at room temperature for 40 h. A small amount of the reaction mixtures (20 uL) were taken to prepare TEM grids.

Preparation of TMV/EDOT-$SO_3^-Na^+$ Composite

TMV (1 mg), EDOT-SO3—Na+ (2 mg) and ammonium persulfate solution (144 uL, 10 mg/mL) were added to a small vial equipped with a stirring bar. Nanopure H2O was added to make the mixture volume to about 1 mL and stirred. The mixtures were adjusted to a series of pH ranging from 4.96 to 8.0 by the diluted HCl and NaOH. The reaction vials were capped and stirred at room temperature. A small amount of the reaction mixtures (20 uL) were taken to prepare TEM grids at 24 h and 74 h.

Preparation of TMV/EDOT-$SO_3^-Na^+$ Composite

TMV (1 mg), EDOT-NH2 (2 mg) and ammonium persulfate solution (2.67 mg) were added to a small vial equipped with a stirring bar. Nanopure $H_2O$ was added to make the mixture volume to about 1 mL and stirred. The original sample pH was about 5.8. The other sample pH was adjusted to pH 8 by the diluted HCl and NaOH. The reaction vials were capped and stirred at room temperature. A small amount of the reaction mixtures (20 uL) were taken to prepare TEM grids at about 24 h.

Example 2

2-Dimensional Nanostructures

2D Self Assembly of Viral Particles at Flat Liquid-Liquid Interface

Spherical HSF and CPMV were successfully self-assembled as a monolayer at the perfluorodecalin-water interfaces. The closely packed CPMV and HSF assembly at interfaces were then crosslinked with glutaraldehyde. These reactions did not disrupt the integrity of the BNP particles. In this study, perfluorodecalin droplets with diameters from 10 to 100 microns were obtained by adding perfluorodecalin into a dispersion of the fluorescently labeled CPMV or HSF in buffer solution, followed by shaking. The particles, dispersed in water, assembled at the perfluorodecalin-water interfaces, stabilizing the dispersion of the water droplets.

The BNP assemblies were thoroughly analyzed. FIG. 15A shows a laser scanning confocal microscope (LSCM) image of a 3D reconstruction of wt-CPMV coated perfluorodecalin droplets after crosslinking with glutaraldehyde and removal of excess particles in the buffer phase by subsequent washing with water. The crosslinking procedure did not change the integrity of the assembly and the resulting capsules were not distorted in shape (see inset). Complete removal of the water and perfluorodecalin disrupted the crosslinked virus shell around the oil phase. Upon rehydration with buffer solution, crumpled shells were observed as shown in FIG. 15B. FIG. 15C depicts a spherical cap generated by assembly and subsequent crosslinking of CPMV particles around a perfluorodecalin droplet sitting on a glass slide. After complete drying of the solvents and washing with buffer and water, the cap folded backwards, revealing distinct wrinkles on the surface. In order to determine the thickness of the crosslinked virus particle assembly, several scanning force microscopy (SFM) images were taken at the edge of the back folded cap. The white box in FIG. 15C indicates the spot where the SFM image in FIG. 15D was taken. Cross-sectional analysis averaging over 256 scan lines yields a step height of 29±2 nm. This is consistent with a monolayer formed by virus particles of 28 32 nm diameter.

Small angle neutron scattering (SANS) was employed to analyze the interfacial assembly of CPMV and shown that the BNP assemblies at the interfaces between perfluorodecalin and H2O/D2O were sheet-like with t=16.5±1.8 nm. This suggests that CPMV formed a monolayer at the interfaces, assuming a uniform scattering length density for the sheets. However, it should be noted that no pronounced inter-particle correlations were seen.

Also, TEM images for the 2-dimensional nanostructures of various viruses are shown in FIG. 16: (a) the hexagonal array of wt-CPMV, (b) the hexagonal array of wt-TYMV, (c) the square array of wt-CPMV, (d) the parallel array of wt-TMV.

Two-Dimensional Films Generated by Water-Oil Interface Assembly

In an aqueous solution (pH 5.8), there were 10 mM 4-morpholineethanesulfonic acid (MES), 150 mM NaCl, 10 mM CdSO4, and 2% glucose (w/v). Then virus stock solution was injected into the aqueous phase to reach a concentration of 0.5 mg/mL. The organic solution is 100 μL 1 mg/mL hexane solution of dehydroabietylamine (DHAA). 2 hours after protein spreading, 5 microliter of the glutaraldehyde solution was added to the aqueous phase. Following a further incubation period of 2 hours, the crosslinked monolayer of 2D ordered virus arrays were formed.

2D Self Assembly of Viral Particles at Flat Liquid-Liquid Interface.

2D flat interface self assembly studies for the spherical viral particles were performed at the heptane-buffer interface. This assembly process resulted in the formation of long range hexagonal patterned arrays of the viral particles. For this experiment the aqueous phase was made by dissolving 10 mM MES, 150 mM NaCl, 10 mM $CdSO_4$ and 2% glucose in nanopure water and the final pH was adjusted in the range 5.3-5.7. To 500 μL of this aqueous phase 0.05 mg/ml virus solution was added. After that on the top of the aqueous phase, a layer of oil phase which consisted of 2 mg/mL solution of DHAA in heptane was spread slowly such that the oil phase made up to 10% of the total volume. DHAA is dehydroabietyl amine which is used as the crystallizing agent and it interacts electro-statically with the viral particles arranged at the interface. After spreading the organic phase the assembly was kept in a saturated heptane atmosphere for two hours for the equilibration. During this equilibration process the viral particles moved to the interface in order to decrease the interfacial energy between heptane and buffer. These organized viral particles were then cross linked using 5 μL of 50% glutaraldehyde solution and the cross linking reaction was carried out for 4 hours. TEM grids were prepared by inserting the grids vertically and picking the layer horizontally up and grids were stained with 2% uranyl acetate solution. The AFM images of the interfacial layer were also recorded. The viral particles formed long range hexagonal arrays at the interface.

Another set of experiments was performed to monitor the self assembly of rod shaped virus particles at the water-PDMS interface. The glass surface was spin coated with a thin layer of polydimethylsiloxane (PDMS). PDMS is a sticky liquid which solidifies under UV exposure for 10 min. This PDMS coated glass slide was incubated with 0.2 mg/mL of rod-shaped virus particle solution. They were incubated overnight at 4° C. in order to achieve equilibrium. Next day, the incubated PDMS slide was exposed to UV for 10 min. to solidify the surface. The solidification of PDMS immobilized the arranged virus particles at the interface. The solidified wafer was washed with water and AFM images were recorded. Surface coverage with virus particles was observed.

Self Assembly of Viral Particles at the Solid-Liquid Interface

To study the assembly of viral particles at solid-liquid interface, silane coated glass slides and PDMS coated slides were used. PDMS slides were made by spin coating PDMS and solidifying it with UV exposure prior to the incubation with the virus solution. These wafers were incubated in 2 mL of 0.2 mg/mL rod shaped virus solution and kept overnight at 4° C. Next day the wafers were washed with nanopure water and AFM analysis were performed. The AFM images showed the virus coverage on the surface of the wafers used. Similar experiment was performed with plain glass slide; the coverage of the plain glass surface with virus particles was less as compared to the other surfaces.

Self Assembly of Viral Particles at Air-Liquid Interface

For this set of experiments a drop of 0.2 mg/mL virus solution (diluted with nanopure water) was placed on a piece of silane coated glass slide and plain glass slide. These slides were left overnight to dry in an incubator with the temperature setting at 37° and 61% relative humidity. The next day the AFM analysis of the slides was done and it showed the full coverage of the silane surface with the virus particles whereas, the coverage on the glass slide was less in comparison.

Example 3

Co-Assembly of Virus Nanoparticles with Silica Precursor Preparation of Silica Precursor The sol was prepared by refluxing 10 g TEOS, 8.86 g EtOH, 13.83 g $H_2O$ and 200 µl 2N HCl at ca. 70° C. for one hour, followed by aging for a whole night to obtain a clear silica sol.

Co-Assemble Bionanoparticles with Silica Sol-Gel Process

The composites were prepared by slowly added virus solution into silica sol with stirring. The composite thin film was obtained by the dip-coating. By pouring the mixture into a glass container, the bulk materials were obtained after two day drying at room temperature. The density of virus embedded in the silica gel could be changed by changing the mass ratio of virus and silica precursor.

As shown in FIG. 20, both spherical virus nanoparticles including TYMV, ferritin and rod-like TMV were used as the template to synthesis the virus/silica composite materials. When TYMV are used as the template, after in situ sol-gel process, most of the virus nanoparticles kept their original sizes and morphologies.

After calcinations at 500° C. for two hours, the mesoporous silica was obtained as shown in FIG. 21*a*. It is clear from the FIG. 21*b* that the spherical shape was maintained, while the size was slightly reduced after calcination. Imprinting of the spherical shape of TYMV within the silica was observed. The $N_2$ adsorption-desorption isotherm obtained on the mesoporous silica powders showed typical type-IV curves with a large $H_2$ hysteresis (FIG. 21*c*). This type of isotherm is characteristic of an open interpenetrating pore system with cage structures. The calcined sample had a $N_2$ Brunauer-Emmett-Teller (BET) surface area of 635 $m^2.g^{-1}$, which is comparable with mesoporous silica with large-pores templated with block copolymer. The pore size distribution centered on 1.9 nm and 3.2 nm, and a pore volume of 0.61 $cm^3g^{-1}$. Considering that the average diameter of TYMV is 28 nm, we surmise that the imprinting of surface knob-like structures of TYMV make major contribution to the larger surface area of resulted in mesoporous silica. Therefore, it might be possible to fine-tune the cavity and shape of the pores at sub-nanometer scale by manipulating the surface of the BNP templates. Ferritin could also be used as the template to synthesis composite materials.

FIG. 21*d* shows the small angle x-ray scattering (SAXS) data of TYMV/silica nanocomposite and mesoporous silica after removal of TYMV by calcination. The SAXS data were fitted using the spherical shell form factor. For the TYMV/silica nanocomposite, it shows an inner radius of 9.0 nm and a wall thickness of 2.5 nm. The data confirm that after embedded into silica TYMV maintains its original shape. It is slightly different from the SAXS data of TYMV in solution, which is likely due to the strong electron density difference between TYMV and silica, compared with TYMV and water. During calcination, the volume of silica shrinks due to the elimination of TYMV and the density change. The SAXS date revealed the pores were monodispersed with a diameter of 20.6 nm. This further confirms that BNPs can be good templates to produce mesoporous silica with controlled pore shape and size.

Another spherical particle, HSF, was also employed as the template for the synthesis of silica nanocomposite materials, and mesoporous silica. Since the HSF encapsulates an iron oxide core, the sol-gel process can assist the dispersion of the iron oxide within the silica. The structures of composites and mesoporous silica were also confirmed with TEM and SAXS analysis. Scanning electron microscopy-energy dispersive angle x-ray analysis indicated a homogeneous distribution of iron inside the HSF-templated mesoporous silica. Many studies have demonstrated that ferritin can be used as nanoreactors for the formation of metal or inorganic nanocrystals. Thereby our method can potentially be used to fabricate mesoporous silica incorporated with a homogeneous distribution of inorganic oxides.

As shown in FIG. 22*a*, TMV was also dispersed in the silica sol, retaining its rod-like morphology after sol-gel process. Furthermore, the alignment of TMV in silica can be controlled by addition of divalent metal cations. When $CdSO_4$ was added into the silica precursor, parallel arrays of TMV were induced (FIG. 22*b*). Upon calcination at 500° C. for 2 hours, mesoporous silica was obtained maintaining the channel-like structure. The $N_2$ adsorption-desorption isotherm of the prepared mesoporous silica after calcination showed a typical type-IV pattern characteristic of many mesoporous materials with the BET surface area of 329 $m^2.g^{-1}$.

Rod-like TMV is an ideal nanoparticle to template synthesis composite materials. As shown is FIGS. 22*a* and 22*b*, the TMV can retain the rod-like morphology after sol-gel process. The TMV was well dispersed in the silica rather than aggregation. The amount of TMV embedded in the silica gel was increased with increasing the TMV concentration. When certain amount of the $Cd^{2+}$ salt were added into the silica precursor before the sol-gel process, the ordered assemble structures were obtained (FIG. 22b).

In summary, a practical and versatile sol-gel process for encapsulating bionanoparticles while maintaining their integrity and morphology was developed. Upon calcination, mesoporous silica with monodispersed large pores were produced with the shape and surface morphology of the bionanoparticles "imprinted" inside the silica. Thus, functional composite materials and mesoporous silica with structurally well-defined pores can be produced.

These and other modifications and variations to the present invention may be practiced by those of ordinary skill in the art, without departing from the spirit and scope of the present invention, which is more particularly set forth in the appended claims. In addition, it should be understood the aspects of the various embodiments may be interchanged both in whole or in part. Furthermore, those of ordinary skill in the art will appreciate that the foregoing description is by way of example only, and is not intended to limit the invention so further described in the appended claims.

What is claimed:

1. A method of making a composite nanofiber comprising:
    assembling a plurality of rod-like viruses to form a wire-like structure such that a head of one rod-like virus is adjacent to a tail of an adjacent virus; and
    polymerizing a plurality of monomers about the wire-like structure to fix the plurality of rod-like viruses together in the wire-like structure, wherein the plurality of monomers comprises monomers having an thiol group.

2. The method as in claim 1, wherein the rod-like viruses comprise tobacco mosaic viruses.

3. The method as in claim 2, wherein the tobacco mosaic viruses comprise wild-type tobacco mosaic viruses.

4. The method as in claim 1, wherein the rod-like viruses comprise functionalized rod-like viruses.

5. The method as in claim 4, wherein the functionalized rod-like viruses comprise o-toluenesulfonic acid modified tobacco mosaic viruses.

6. The method as in claim 4, wherein the functionalized rod-like viruses comprise alkyne-functional rod-like viruses.

7. The method as in claim 1, further comprising functionalizing the rod-like viruses.

8. The method as in claim 1, further comprising functionalizing the wire-like structure.

9. The method as in claim 1, wherein the rod-like viruses self-assemble.

10. A method of making a composite nanofiber comprising:
    assembling a plurality of rod-like viruses to form a wire-like structure such that a head of one rod-like virus is adjacent to a tail of an adjacent virus, wherein the rod-like viruses comprise functionalized rod-like viruses, wherein the functionalized rod-like viruses comprise o-toluenesulfonic acid modified tobacco mosaic viruses; and
    polymerizing a plurality of monomers about the wire-like structure to fix the plurality of rod-like viruses together in the wire-like structure.

11. The method as in claim 1, wherein the plurality of monomers comprises positively charged monomers.

12. The method as in claim 1, wherein the plurality of monomers comprises monomers having an amino group.

13. The method as in claim 1, wherein the plurality of monomers comprises aniline.

14. The method as in claim 13, wherein polymerizing the plurality of monomers forms polyaniline about the wire-like structure.

15. The method as in claim 10, wherein polymerizing the plurality of monomers forms polyaniline, polypyrole, polythiophene, polyethylenedioxythiophene, polypyrazole, or derivatives or copolymers thereof.

16. The method as in claim 10, further comprising functionalizing the rod-like viruses.

17. The method as in claim 10, further comprising functionalizing the wire-like structure.

18. The method as in claim 10, wherein the rod-like viruses self-assemble.

19. A method of making a composite nanofiber comprising:
    assembling a plurality of rod-like viruses to form a wire-like structure such that a head of one rod-like virus is adjacent to a tail of an adjacent virus, wherein the rod-like viruses comprise functionalized rod-like viruses, wherein the functionalized rod-like viruses comprise alkyne-functional rod-like viruses; and
    polymerizing a plurality of monomers about the wire-like structure to fix the plurality of rod-like viruses together in the wire-like structure.

20. The method as in claim 19, further comprising functionalizing the rod-like viruses.

21. The method as in claim 19, further comprising functionalizing the wire-like structure.

22. The method as in claim 19, wherein the plurality of monomers comprises positively charged monomers.

23. The method as in claim 19, wherein the plurality of monomers comprises monomers having an amino group.

24. The method as in claim 19, wherein the plurality of monomers comprises aniline.

25. The method as in claim 24, wherein polymerizing the plurality of monomers forms polyaniline about the wire-like structure.

26. The method as in claim 19, wherein polymerizing the plurality of monomers forms polyaniline, polypyrole, polythiophene, polyethylenedioxythiophene, polypyrazole, or derivatives or copolymers thereof.

27. The method as in claim 19, wherein the rod-like viruses self-assemble.

* * * * *